US007860726B2

(12) United States Patent
Connely, III et al.

(10) Patent No.: US 7,860,726 B2
(45) Date of Patent: Dec. 28, 2010

(54) METHOD FOR PROVIDING WEB-BASED DELIVERY OF MEDICAL SERVICE REQUESTS

(75) Inventors: Robert Emmitt Connely, III, Roswell, GA (US); Alok Mathur, Alpharetta, GA (US); Steven Troy Ordahl, Alpharetta, GA (US); Andreas Achille Piccolo, Gainesville, GA (US)

(73) Assignee: McKesson Information Solutions LLC, Alpharetta, GA (US)

( * ) Notice: Subject to any disclaimer, the term of this patent is extended or adjusted under 35 U.S.C. 154(b) by 1494 days.

(21) Appl. No.: 10/941,604

(22) Filed: Sep. 15, 2004

(65) Prior Publication Data
US 2005/0060201 A1    Mar. 17, 2005

Related U.S. Application Data

(60) Provisional application No. 60/503,276, filed on Sep. 15, 2003.

(51) Int. Cl.
G06Q 10/00    (2006.01)
G06F 19/00    (2006.01)
(52) U.S. Cl. .............................................. 705/2; 705/3

(58) Field of Classification Search .................. 705/2–3, 705/5; 600/300; 348/14.01
See application file for complete search history.

(56) References Cited

U.S. PATENT DOCUMENTS

| 5,771,511 | A |   | 6/1998 | Kummer et al. ................. 5/600 |
| 5,772,585 | A | * | 6/1998 | Lavin et al. .................. 600/300 |
| 5,960,404 | A |   | 9/1999 | Chaar et al. ..................... 705/8 |
| 6,046,761 | A | * | 4/2000 | Echerer ................... 348/14.01 |
| 6,094,676 | A |   | 7/2000 | Gray et al. ................... 709/217 |
| 2002/0026329 | A1 | * | 2/2002 | Saito et al. ...................... 705/3 |
| 2002/0035493 | A1 | * | 3/2002 | Mozayeny et al. ............. 705/5 |
| 2004/0034550 | A1 | * | 2/2004 | Menschik et al. ............... 705/3 |

OTHER PUBLICATIONS www.ups.com/tracking from www.archive.org, Sep. 9, 2002.*

* cited by examiner

*Primary Examiner*—Luke Gilligan
*Assistant Examiner*—Joseph Burgess
(74) *Attorney, Agent, or Firm*—Alston & Bird LLP

(57) ABSTRACT

A method for improving communication in the delivery of healthcare services is described. Also disclosed is a method of improving the area of Pre-Service operations. The method may utilize the ePackages described herein.

22 Claims, 36 Drawing Sheets

Access Patient Information

User is checking the patient out and entering charges

Figure 9

MCKESSON
*Empowering Healthcare*

Integrate data into ePackage Form

- User may manually enter data to complete form
- An optional feature moves the information from the practice management application into the form

Figure 11

Capture Images from Physician Office

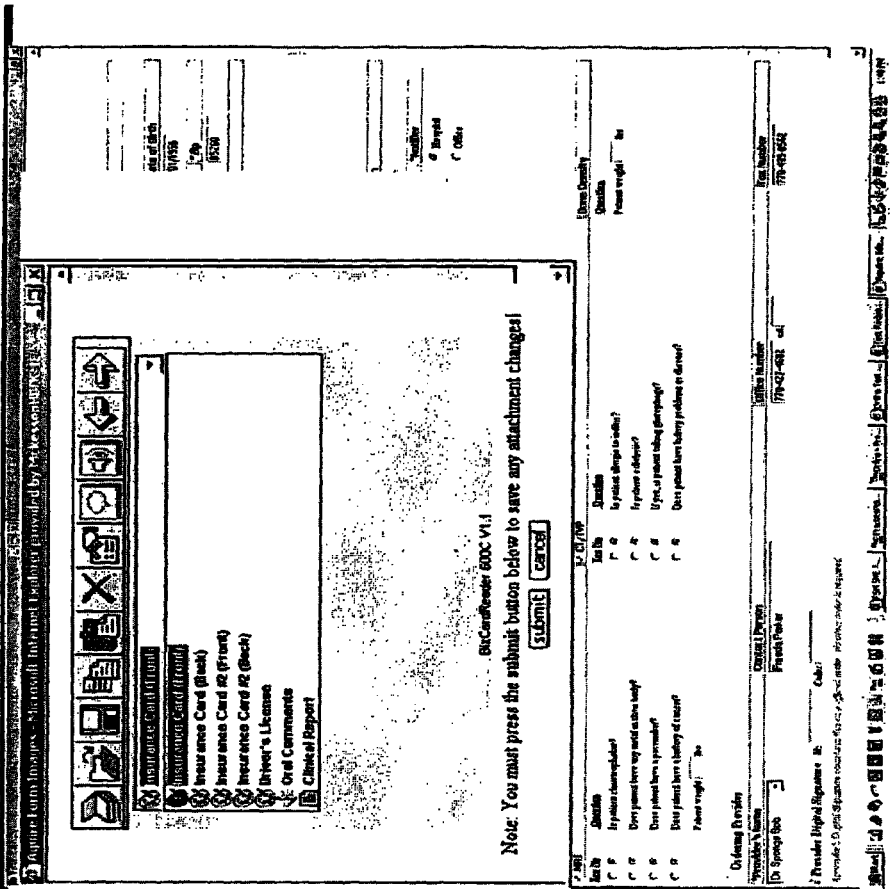

- Digital scans of insurance cards and drivers licenses can also be added to the Pre-Service Manager e-Package
  - Any TWAIN compliant scanner is supported
  - Simple card scanners make it easy to capture valuable information from the physician's office
- Other scanned documents like clinical notes and charts can be added to the e-Package
- Voice files may be included for clarification of instructions
- Stored images may be included as well as screen captures

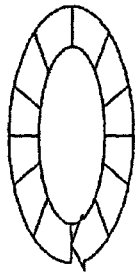

Figure 12

Select Diagnosis Codes

- The nurse selects diagnosis codes or searches by description
- Multiple codes can be added to any one request form
- Pre-Service Manager includes the utilities to manage the distribution and updates of code tables
- Reduces errors and transpositions of codes
- Reduces time to find and specify correct code

MCKESSON
*Empowering Healthcare*

Figure 14

Select Facility or Service Location

Nurse enters patient preferences.

Provide Scheduling Information

- Scheduling detail is added
  - A pop-up calendar makes it easy to select a preferred date
  - Pull-down list makes it easy to select a preferred day
  - Pull-down list makes it easy to select a preferred time of day
- Patient contact information can also be added

Add Instructions or Comments

- The "Comments" text entry box enables threaded communications throughout the life of the electronic package
  - Physicians and staff can enter patient detail or special requests
  - Scheduling can add pre-test instructions and materials
  - Pre-service personnel can ask questions and obtain further information without disruptive phone calls
  - All of the conversations are available when the patient shows up for the service

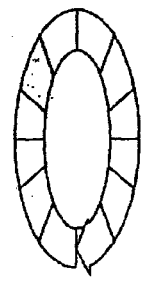

Figure 17

Select Physician and e-Sign

- The e-Package identifies the ordering physician.
- The physician's electronic signature can be applied at this time, or later through the Horizon*WP* Physician Portal.
- This flexibility ensures that a signature is obtained prior to patient arrival...no matter where the physician is

MCKESSON
*Empowering Healthcare*

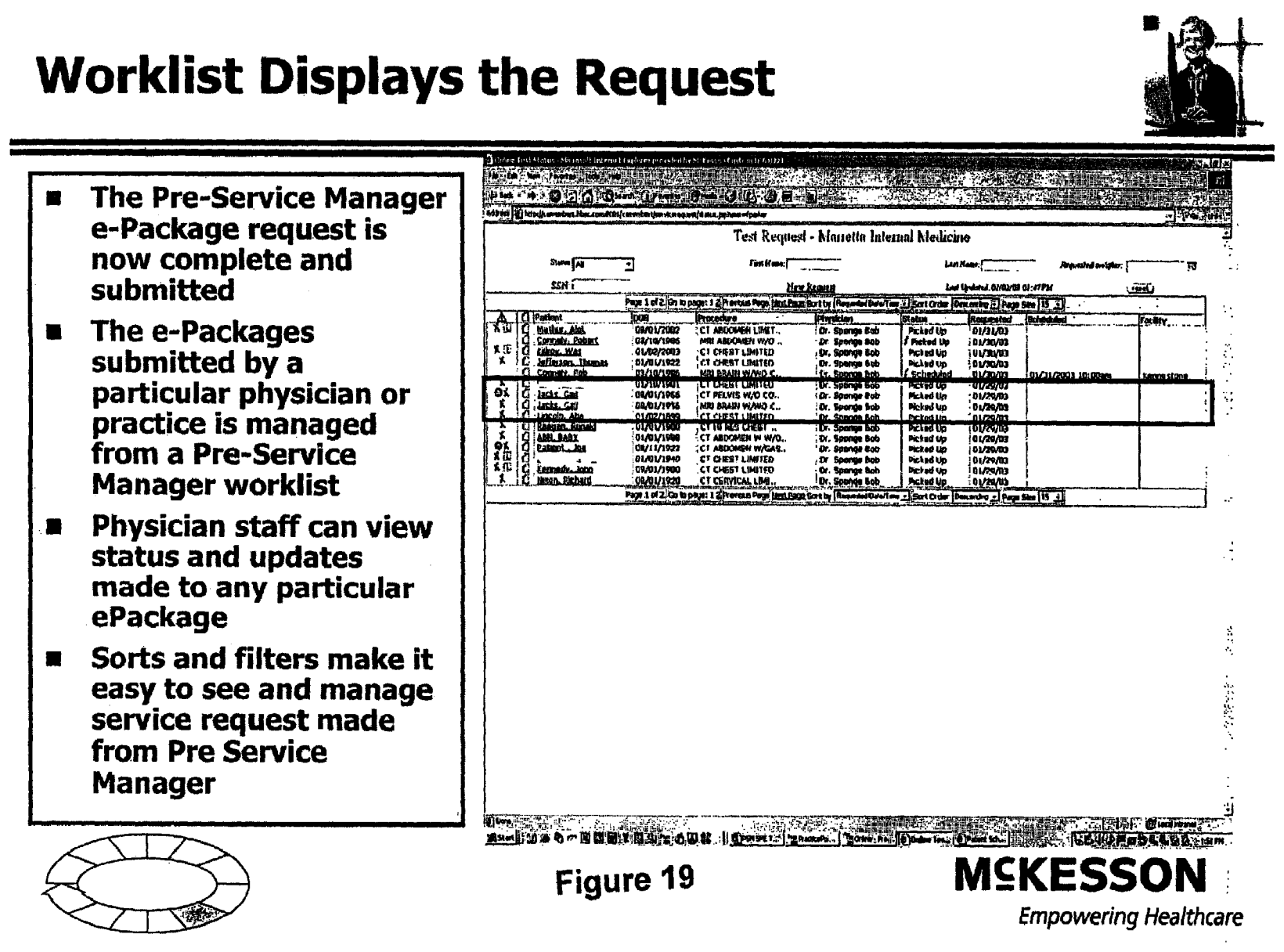

Worklist Displays the Request

- The Pre-Service Manager e-Package request is now complete and submitted
- The e-Packages submitted by a particular physician or practice is managed from a Pre-Service Manager worklist
- Physician staff can view status and updates made to any particular ePackage
- Sorts and filters make it easy to see and manage service request made from Pre Service Manager

Figure 19

Scheduling Views Service Requests in Worklist

- In the hospital, the scheduler also has a Pre-Service Manager worklist
  - It can run as a stand alone Web site
  - Or through HPP
- The worklist is filtered to show request requiring scheduling attention
- Selecting a patient to work locks the e-Package until the update is complete

Figure 21

Patient Identification

- The scheduler first needs to identify the patient
- The user navigates to the Patient Search area of the application

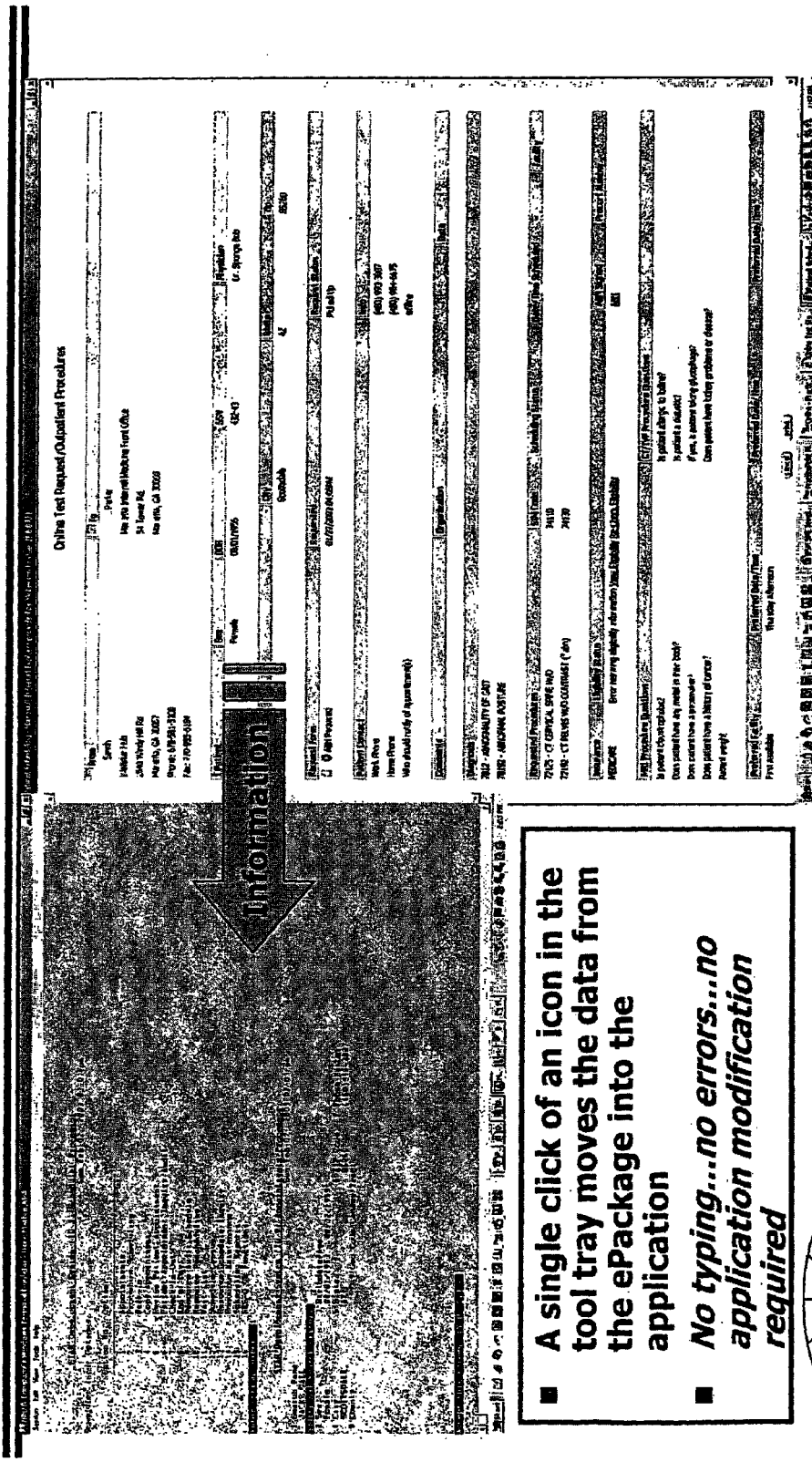
Figure 23

Update ePackage with Scheduling Info

- Information generated in the scheduling application is added to the ePackage
- Comments and instructions can also be added

Figure 24

Check Eligibility, Address and Credit

- The eligibility service is provided from McKesson's Transaction Solutions Hub

- Clicking on the "Eligibility" link does the following:
    - Collects information from the ePackage relevant to the eligibility request
    - Sends a Web services request to the TSH
    - Returns eligibility results (in PDF format) for inclusion in the ePackage

- Credit check and address verification are also planned services offered by the TSH

Figure 25

Check Medical Necessity and Create ABN

- Pre-Service Manager also enables information in the e-Package to be used to perform medical necessity and code audits through Pathways Compliance Advisor

- Pre-Service Manager works with e-Pad technologies to allow patient's to electronically sign the ABN

- Users may also print the PDF for patient signature

MCKESSON
*Empowering Healthcare*

Figure 26

METHOD FOR PROVIDING WEB-BASED DELIVERY OF MEDICAL SERVICE REQUESTS

CROSS REFERENCE TO RELATED APPLICATIONS

This application claims priority to U.S. Provisional Application Ser. No. 60/503,276 filed Sep. 15, 2003, incorporated by reference in its entirety herein.

BACKGROUND OF THE INVENTION

1. Field of the Invention

The present invention relates a method for improving communication in the delivery medical services. More particularly, this invention relates to a method to enhance communication and perform tasks to assist medical professionals in patient care, especially in the area of Pre-Service.

2. Description of the Related Art

In the world of healthcare is a geographically and organizationally independent collection of many constituents, such as the following: hospitals and healthcare enterprises; physicians (group or small practices) and clinics; patients and consumers; payors and government (Medicare, Medicaid, etc.); pharmacies and other suppliers; home health agencies; knowledge sources and educational institutions. These constituents work together in highly dynamic relationships. As such, these constituents must share highly confidential information to conduct complex processes (e.g. surgical procedures, radiology exams, lab tests, prescription fulfillment and others). It is imperative that some information be readily available to these constituents.

Today, these relationships exchange information using conventional methods such as paper, phone and human courier methods almost exclusively. It is believed that these inefficient methods represent a significant cost to the healthcare system as a whole. It has been estimated that $600B of the $1.4T national healthcare expense consists of administrative costs like these.

One area of communication in which this problem may be exacerbated is in the "Pre-Service" arena. "Pre-Service" may be defined as the events that take place prior to a patient receiving services from the hospital. These events may typically involve hospital and non-hospital personnel and resources, such as physicians, physician office staff, hospital scheduling departments, pre-certification professionals, and department registration staff.

FIGS. 1A-C show the events that may occur during a typical Pre-Service event ("Pre-Service"). First, a physician makes a decision to refer a patient, to a hospital, for example. Patient information is collected, usually by the physician's office staff such as a nurse. The type of service prescribed by the physician is determined and collected. Other information, such as preferred appointment dates, may be collected at this time. The physician request is signed, as required in most instances.

Referring to FIG. 1B, the patient is scheduled at the hospital to which the patient has been referred. The hospital is provided with the Pre-Service instructions. The patient may pre-register, including information about preferred appointment dates for the procedure to be performed. The information from the patient is delivered and the hospital performs Pre-Services checks and verification. This is typically performed by the hospital Pre-Service personnel.

As shown in FIG. 1C, the patient then signs a consent for the procedure, the patient is registered by hospital registration, and the prescribed service is later performed.

Prior art systems may have detrimental financial impacts on the health-care provider, such as the denials of benefits from insurance companies, and under-utilization of resources. Prior art systems may also include inefficiencies, such as waste and duplication of effort, incomplete information, etc. all of which may impact the quality of patient care, lead to patient dissatisfaction, and lead to staff dissatisfaction.

One typical prior art system is shown in FIG. 2. As can be seen and as described above, communication (telephonic, fax, and mail) is exchanged among a myriad of constituents: physician's office, hospital scheduling, patient, hospital Pre-Service, hospital registration, e.g. The inefficiencies in prior art communication techniques cause detrimental effects on the care of the patient. It has been estimated that 20% of the costs associated with pre-servicing can be reduced if the information and communications are improved.

Many attempts to solve these problems have been attempted in the past (CHINs, Web, etc.). Examples include CHINs (community health information networks) and utilizing the web. However, these methods may provide un-secured communication between the constituents and may incur the same deficiencies of the prior art, partly because the technologies available at the time were insufficient due to many factors including cost, ownership, centralization and complexity. In short, in the prior art methods, computing technology may have been unable to operate effectively in the highly complex healthcare world.

The present invention provides a solution that may minimize, or eliminate, the problems associated with the prior art solutions. The disclosed method provides a more reliable, highly secure communication and workflow mechanism than that presently known in the prior art. The method reduces the need to rely upon the traditional, inherently fallible and unsecured communication mechanisms and couriers of paper, phone and fax.

SUMMARY OF THE INVENTION

The invention relates to a method of improving communication between healthcare providers in a secure fashion, particularly when performing the Pre-Service function. In some aspects, an infrastructure is described having a transport mechanism and a packaging mechanism, such as an epackage, to facilitate the communication between providers of healthcare. In some embodiments, flow between desperate healthcare constituents involved in a request for medical service transaction is improved. Specifically, the reduction of the traditional communication methods of paper, phone and fax as well as the inherently fallible transportation mechanisms used to courier sensitive medical information. In some embodiments, the invention very loosely couples self-describing "electronic packages" or "ePackages." These ePackages can contain electronic documents, computer objects and multimedia streams which have an aggregate ability to describe the request for medical service and provide some or all supporting content needed for the fulfillment of the request by the service provider, as summarized in FIG. 3. Also described is a peer computing infrastructure for the delivery and synchronization of ePackages among the various healthcare constituents involved in the request for service process over the internet.

BRIEF DESCRIPTION OF THE DRAWINGS

FIG. 9-27 show screen shots of the step being performed of various embodiments of the present invention.

Figure 1A:
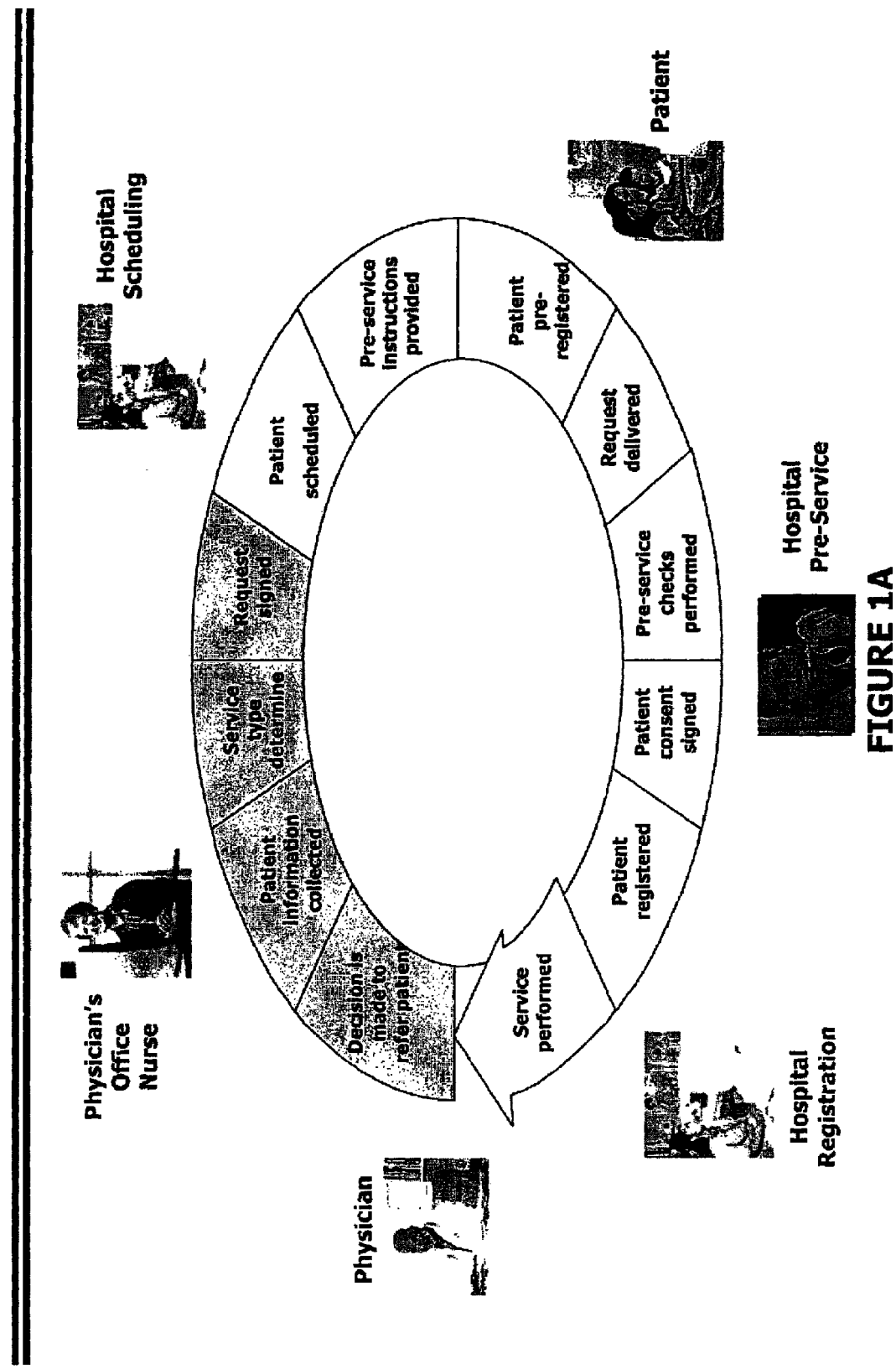
FIGS. 1A-C show events in a typical Pre-Service.
Figure 1B:
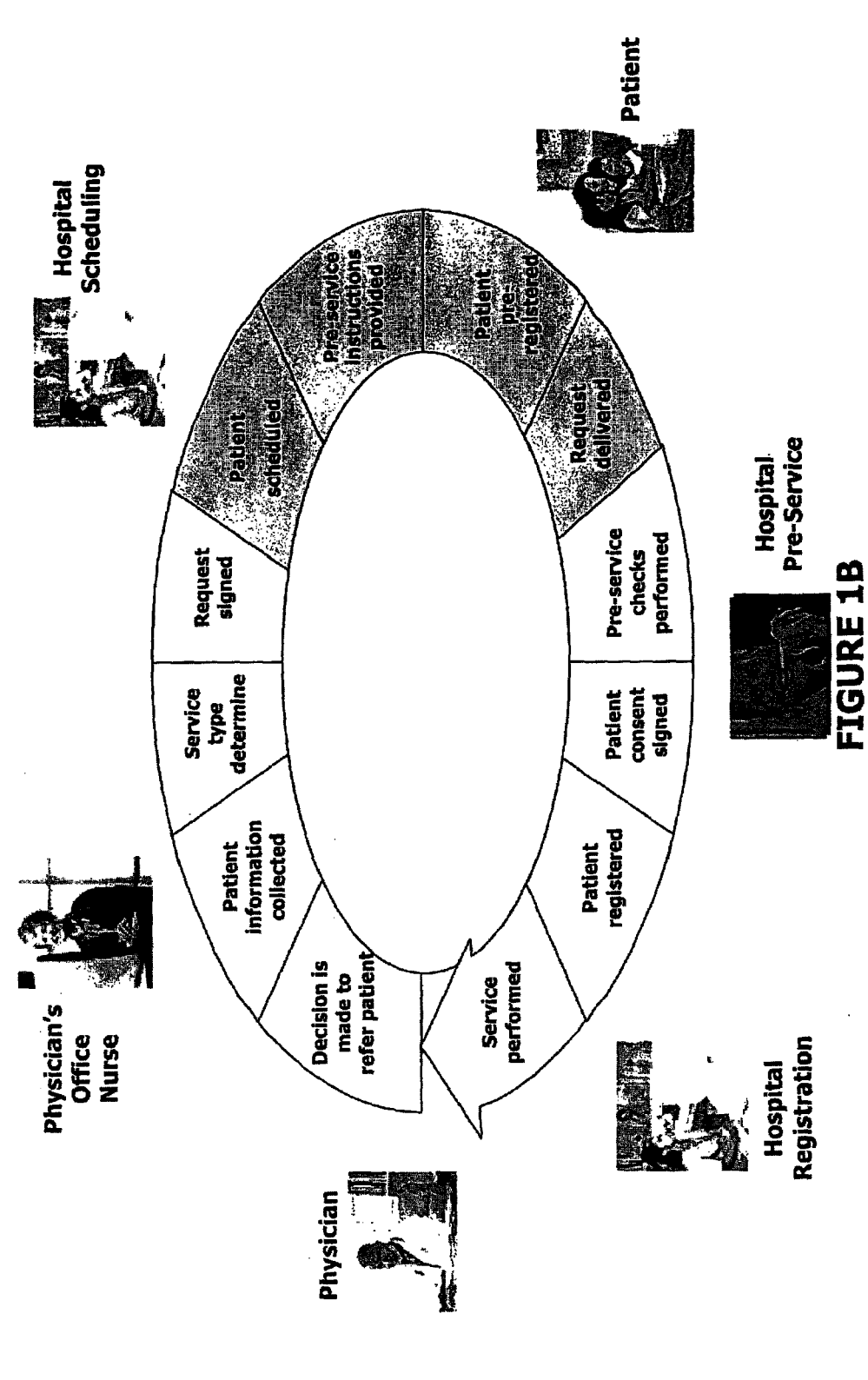
Figure 1C:
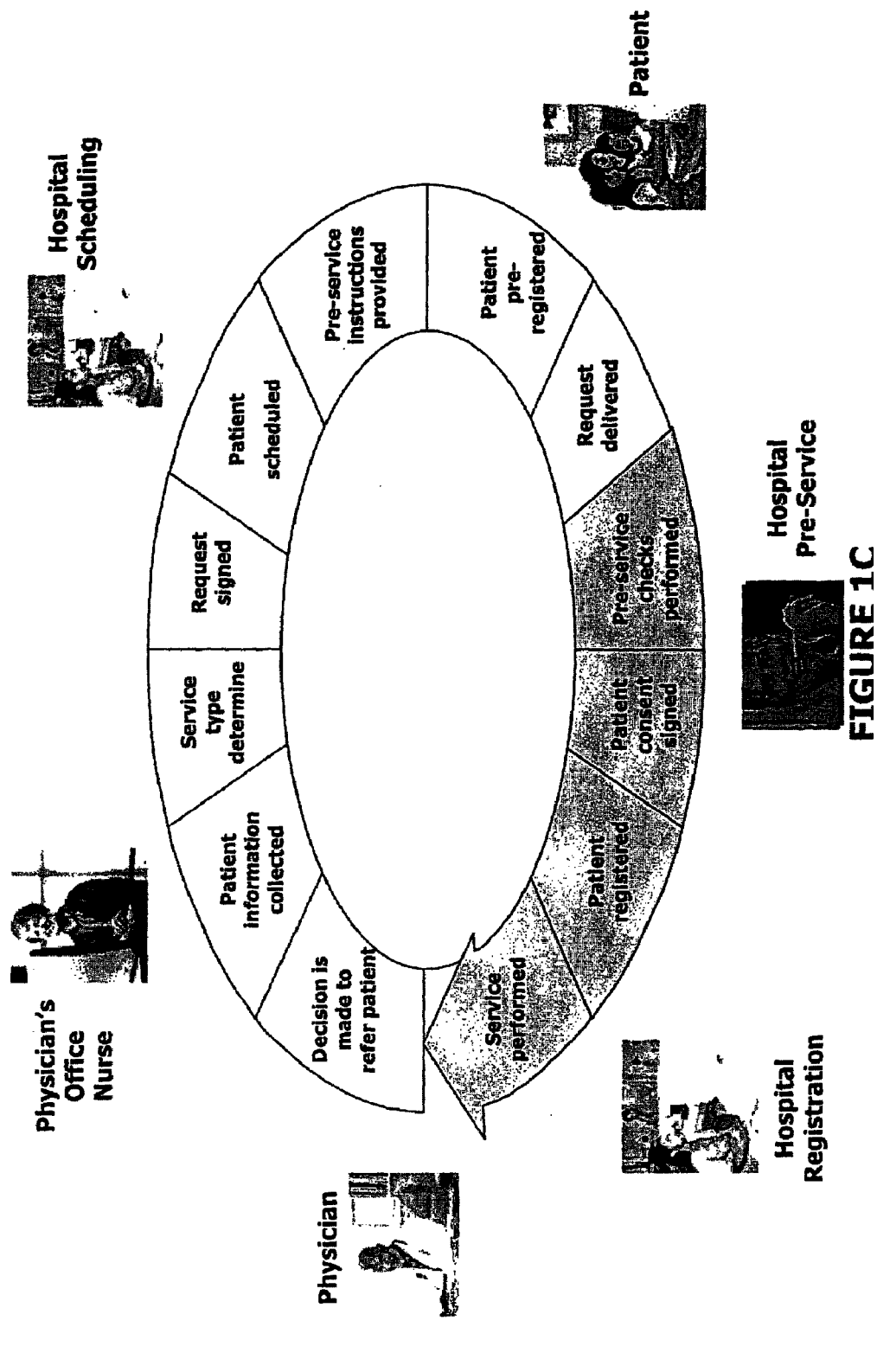
Figure 2:
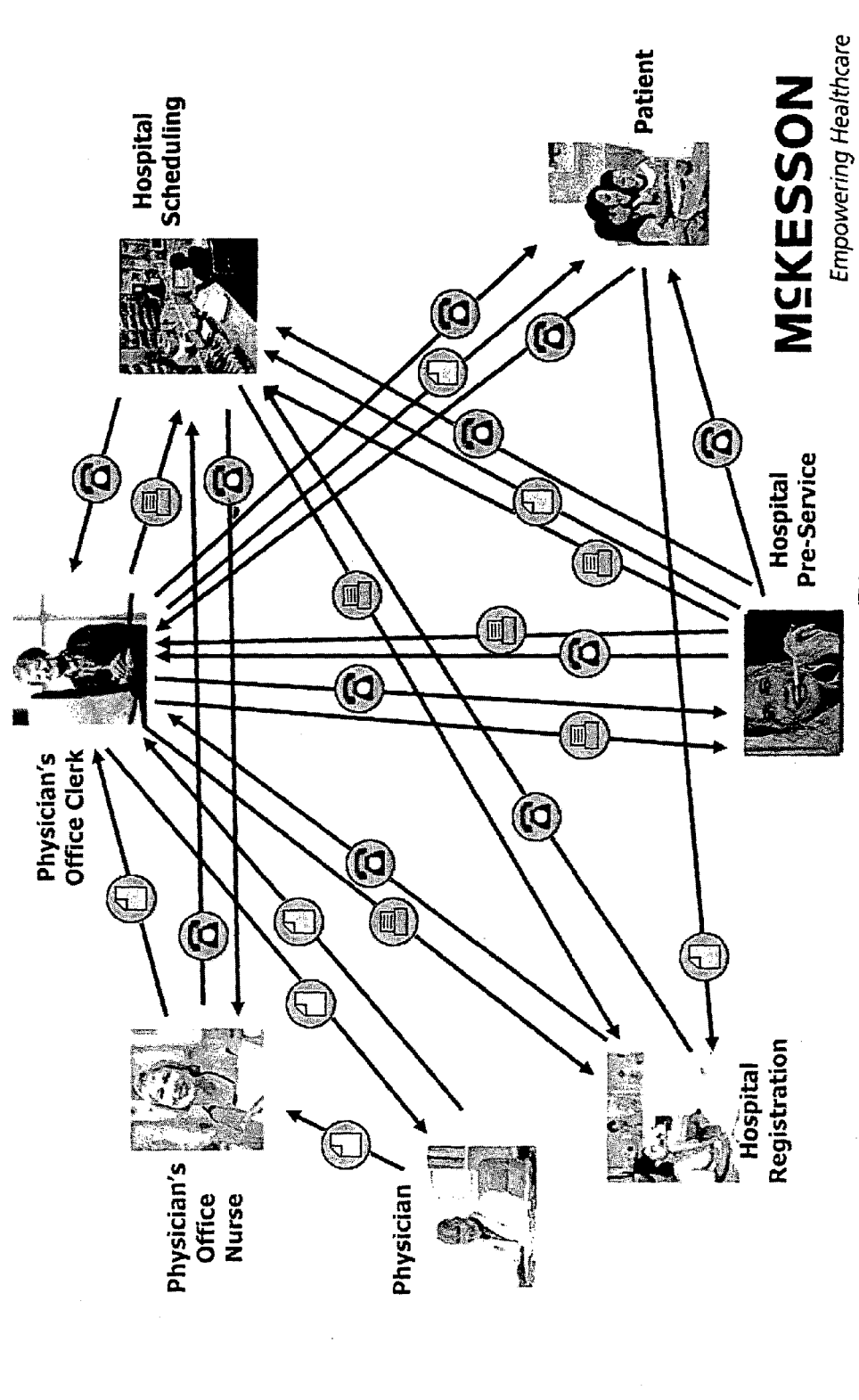
FIG. 2 shows a prior art method of Pre-Service.
Figure 3:
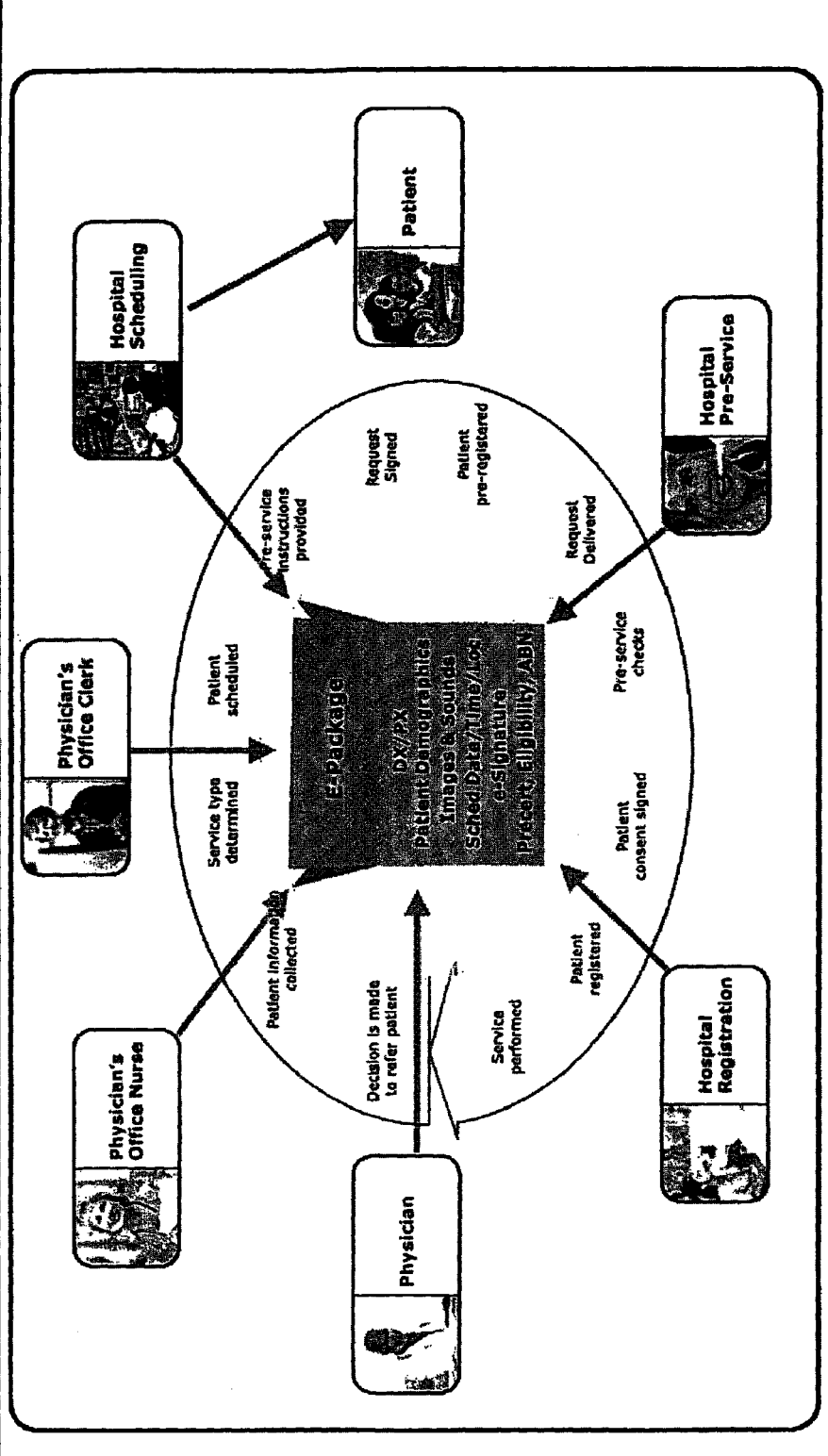
FIG. 3 shows an overall Pre-Service process of one embodiment of the present invention in which the Pre-Service is enhanced utilizing an ePackage.

While the invention is susceptible to various modifications and alternative forms, specific embodiments have been shown by way of example in the drawings and will be described in detail herein. However, it should be understood that the invention is not intended to be limited to the particular forms disclosed. Rather, the intention is to cover all modifications, equivalents and alternatives falling within the spirit and scope of the invention as defined by the appended claims.

DESCRIPTION OF ILLUSTRATIVE EMBODIMENTS

Illustrative embodiments of the invention are described below as they might be employed in providing health care services. In the interest of clarity, not all features of an actual implementation are described in this specification. It will of course be appreciated that in the development of any such actual embodiment, numerous implementation-specific decisions must be made to achieve the developers' specific goals, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following description and drawings.

Embodiments of the invention will now be described with reference to the accompanying figures.

BACKGROUND

To accomplish the above tasks, a computer network infrastructure (the "Infrastructure") is described in the following embodiments. The Infrastructure may utilize JXTA peer-to-peer computing architecture. The Infrastructure may enable Nodes running the Infrastructure to communicate securely over the Internet. Every Node can exchange information with any Node of which it is aware.

The Infrastructure may utilize outgoing http connections for communication. The payloads may be encrypted during transmission. The payloads may be encrypted at rest. The security keys may be generated by the Infrastructure itself. The payloads may be anything a Java program can stream, including the ePackages described herein.

One aspect of the present invention involves an "ePackage" Application Program Interface ("API") (i.e. a set of routines that an application programmer uses to request a carry out lower-level services performed by a computer's operating system), which allows applications to easily create, send and receive electronic packages. The Infrastructure enables running of lightweight applications on Nodes distributed across the Internet.

The fundamental unit of the architecture is the Node. Nodes are deployed across the Internet and communicate with each other using the infrastructure. Each Node requires a J2EE compliant Application Server. This allows Nodes to host applications. These applications interact with their counterparts on other Nodes using the communication features of the infrastructure.

The Infrastructure may use a packaging mechanism that utilizes the ePackage, which is an abstraction over the underlying TCP/IP network.

Every Node may consist of the following five components: (1) a Java virtual machine—Sun Reference Implementation 1.3.1; (2) An Application Server—The type of application server used by a Node may depend on the volume expected on the Node. When large volumes of Nodes are utilized, e.g. deployed in hospitals, strong servers like WebLogic may be utilized. When smaller Nodes, e.g. in single physician practices are utilized, lightweight application servers may be utilized. (3) A date store. Just like the type of application server may depend on the volume, the choice of data store may be based on the volume of transactions expected on the Node. Any JDBC compliant database may be supported, such as Oracle to Hypersonic SQL. The data store can also be the native file system of the Node. (4) The Infrastructure Software to communicate with other Nodes across the Internet; and (5) Optional applications hosted by the Node.

Figure 4:
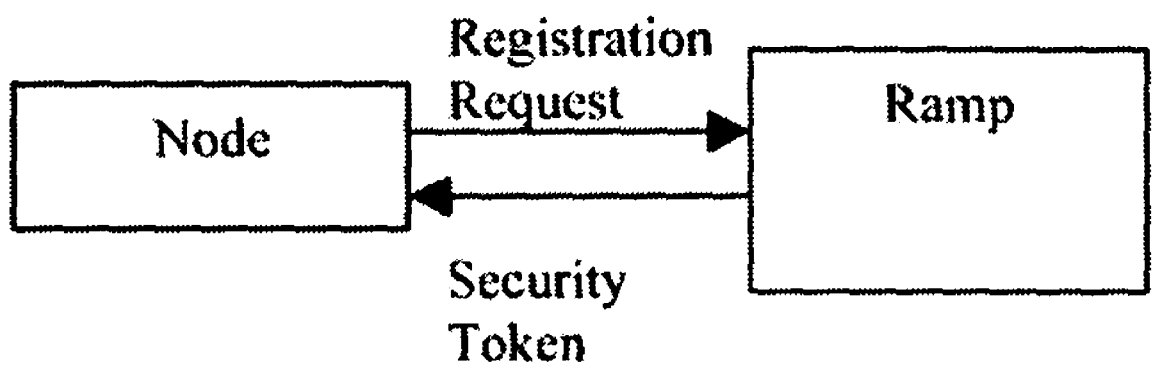
FIGS. 4-6 detail the prior art Infrastructure.

The following describes the transport mechanism of some embodiments of the present invention. Every Node has to be registered to be operational. The registration and future communication may have a rendezvous server called the Ramp, as shown in FIG. 4.

Once Infrastructure Software is installed on a Node machine, the following steps take place to complete its registration:

1. Node sends a registration request to Ramp. This communication takes place using https. The Node provides its identity information.
2. The Node repeatedly tries to get its registration request fulfilled by communicating with the Ramp, again over SSL.
3. When the request to register the Node is granted on the Ramp, the Ramp generates a security token specific to the Node. The Ramp sends a copy to the Node the next time the Node tries to get its registration request fulfilled. The Ramp saves a copy of the token internally.
4. The Node files the token internally.

The connectivity between Nodes is asynchronous. Nodes do not connect with each other. Instead they connect only with their Ramp. The Ramp accepts messages from Nodes and delivers them to other Nodes when they connect.

The connection from Nodes to Ramp is done over http. Nodes initiate the connections. No holes have to be drilled in firewalls, as the Nodes need only outgoing http access.

Figure 5:
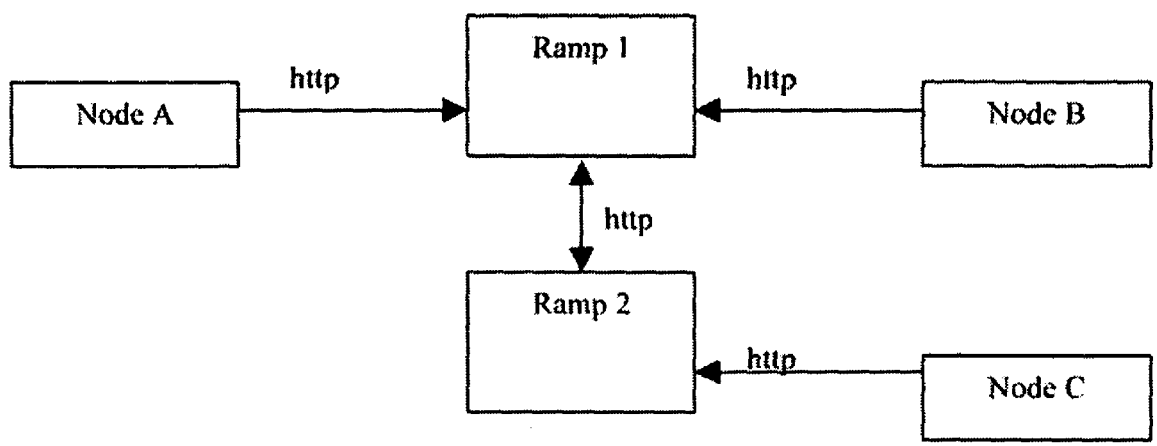

The Ramps can be chained together. In FIG. 4, Ramp 2 is acting like Node C to Ramp 1. Similarly, Ramp 1 is being the proxy for Node A and Node B with Ramp 2, as shown in FIG. 5.

Figure 6:
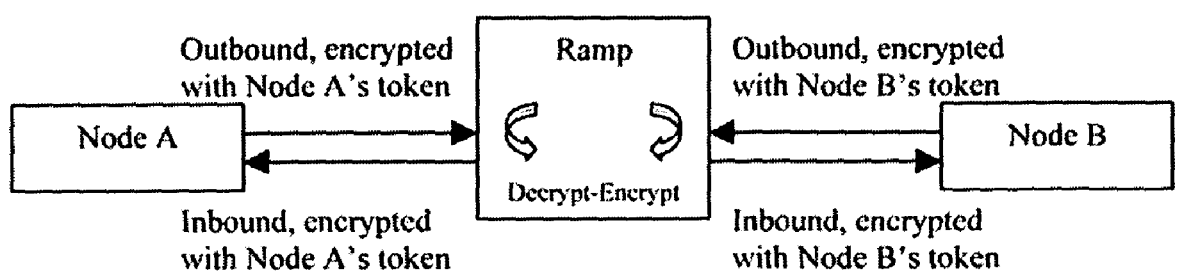

Referring to FIG. 6, the Transportation of payloads between Nodes is shown. Every Node, at some configurable interval, attempts to make an http connection with its Ramp. If the connection is successful, the following events take place:
1. The Node hands over, to the Ramp, any payloads destined for other Nodes, encrypted with the Node's security token.
2. The Ramp stores them in its own queue.
3. The Ramp hands over, to the Node, any payloads destined for the Node—waiting for the Node in its in-bound queue, encrypted with the Node's security token.
4. The Ramp works on its internal queue:
a. Picks a payload from its queue,
b. Decrypts it with the Source Node's security token,
c. Determines the Destination Node,
d. Encrypts the payload with the Destination Node's security token and
e. Puts the encrypted payload in the Destination Node's in-bound queue on the Ramp.

The Packaging Mechanism of one embodiment of the present invention is described hereinafter as an "ePackage." Although the Transport Mechanism works on payloads that can be any streamed Java objects, from an applications' point of view, the communication quantum is the ePackage. The ePackage may be considered to be an abstraction above the payloads of the Transportation Mechanism.

The Packaging Mechanism provides the following:
1. Routing and Mailing list functions;
2. Auditing and tracking functions;
3. Object and stream handling functions;
4. Invocation of Application supplied handlers; and
5. Utilization of the underlying TCP/IP transport mechanism.

Figure 7:
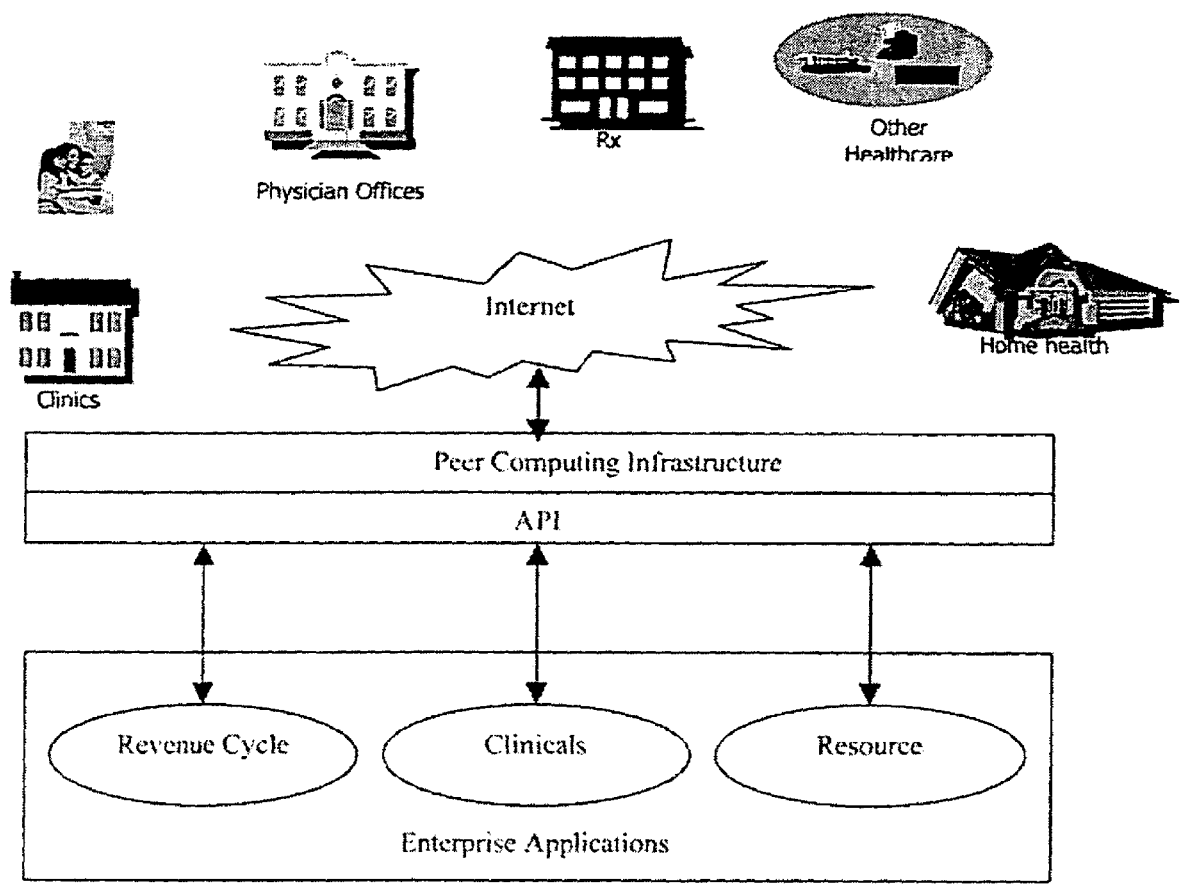
FIG. 7 shows the ePackage API.

As shown in FIG. 7, applications can view the Infrastructure as a gateway to communicate with systems that are outside the network. The Infrastructure provides a means for such applications to get loosely coupled with other applications in the healthcare world.

The Infrastructure may also provide the operating system to deploy lightweight applications and make them prevalent in the healthcare real world.

The following describes the ePackage API.

---

6.1 com. mckesson. product.camembert.edelivery
Class ePackage
java.lang.Object
    |
    +--com.mckesson.product.camembert.edelivery.ePackage
All Implemented Interfaces:
    com.mckesson. util. io. index.indexable, java. io. Serializable
public final class ePackage
extends java.lang.Object
implements com.mckesson.util.io.index.Indexable, java.io.Serializable

---

The ePackage is a collection of objects used to deliver and receive information electronically between organizations or sites. It is comprised of the following objects:

Package Header—Contains information primarily used to track date sensitive information about the ePackage. This information is managed internally by the infrastructure.

Destination—This is the node and the associated organization/individual for which the ePackage is to be delivered. An application constructs a destination object using the Package Manager, which in turn is used as an input to constructing an ePackage.

Source—This is the node and the associated organization/individual from which the ePackage originated. An application constructs a source object using the Package Manager, which in turn is used as an input to constructing an ePackage.

Tracking History—This is a collection of Tracking Activity objects that contains the movement log of the ePackage between destination and source nodes. The Tracking History is managed internally by the infrastructure.

Workflow History—This is a collection of Workflow Activity objects which contains application specific state information regarding the ePackage. Application state information can be used to capture data about the application to generate workflows or worklists as the ePackage is sent and received between its source and destination. The Workflow History is managed by the application.

Packing List—This is a collection of Item objects that contains the attachments to the ePackage. Attachments are fed to the ePackage by the application as InputStreams, or Objects. They can consist of any valid type supported as Java streams, or objects. If an application uses an object as an attachment, the object must implement the Java Serializable interface. Typically, the attachments are used to support the applications' data requirements as the ePackage is sent and received between its source and destination. The Packing List is managed by the application.

The following is an example of how an ePackage is constructed and submitted for processing in one embodiment of the present invention:

---

```
import com.mckesson.product.camembert.edelivery.*;
try {
    // Obtain Source and Destination Objects
    DestinationInput di = new DestinationInput("wellstar",
"windyhill It, "scheduling", "bsmith", "sampleapplication", "Betty Smith");
    Destination destination = TargetHelper.getDestination(di);
    Source Input si = new SourceInput("12345", "sampleapplication");
    Source source = TargetHelper.getSource(si);
    // Construct the ePackage
    epackage epx = new ePackage(source, destination);
    // Add Workflow Items
    WorkflowActivity wa = new WorkflowActivity( );
    wa.add("form", "signed", "false");
    wa.add("request_1", "status", "Requested");
    wa.add("request_1", "lastUpdated", "11/11/2002 12:29PM");
    String key = epx.add(wa);
    // Create the Packing List
    String[ ] comments = new String[2];
    comments [0] = "attached is a vector";
    comments [1] = "it implements Serializable";
    Vector v = new Vector( );
    for (int i=1; i<11; i++) {
        v.addElement("Some data line" + i);
    }
    Item itx = new Item("Radiology Requests Application",
                        "vector",
                        "application/object",
                        "",
                        "",
                        comments,
                        null,
                        v) ;
    epx.add(itx);
    // Send the ePackage
    PackageManager.send(epx);
}
catch (Exception e) {
    System.out.println(e);
}
```

The ePackage is placed in the logical outbox for the specified destination.

The following tables summarize the ePackage contents.

| Field Summary | |
|---|---|
| static java.lang.String | APPLICATION |
| static java.lang.String | CREATIONDATE |
| static java.lang.String | DESTINATION |
| static java.lang.String | EPACKAGE |
| static java.lang.String | LASTSTOREDDATE |
| static java.lang.String | PACKAGES |
| static java.lang.String | PRIORITY |
| static java.lang.String | QUEUE |
| static java.lang.String | SOURCE |
| static java.lang.String | VERSION |
| static int | ERROR |
| static int | IN |
| static int | NONE |
| static int | OUT |

| Constructor Summary |
|---|
| ePackage( )<br>    Default constructor |
| ePackage(ePackage epackage)<br>    Copy Constructor |
| ePackage(Source src, Destination dest)<br>    Constructor used to create a new ePackage when the Source and Destination objects are supplied. |

| Method Summary | |
|---|---|
| java.lang.String | add(Item item)<br>    Adds or updates a Packing List Item object for the ePack |
| java.lang.String | add(TrackingActivity trackingActivity)<br>    Adds or updates a Tracking Activity object for the ePack |
| java.lang.String | add(WorkflowActivity workflowActivity)<br>    Adds or updates a Workflow Activity object for the ePackage. |
| java.util.Date | getCreationDate( )<br>    Returns the create date and time for the ePackage |
| Destination | getDestination( )<br>    Returns the destination object for the ePackage. |
| java.lang.String | getId( )<br>    Returns the globally unique package identifier for the ePackage |
| com.mckesson.util.io.index.Index[ ] | getIndexCollection( ) |
| Item | getItem(java.lang.String key)<br>    Returns an individual Packing List Item object by passing in its internal key. |
| Item | getLastItem( )<br>    Returns the Last item for the ePackage |
| java.util.Date | getLastStoredDate( )<br>    Returns the date and time last saved for the ePackage |
| TrackingActivity | getLastTrackingActivity( )<br>    Returns the Last Tracking Activity for the ePackage |
| WorkflowActivity | getLastWorkflowActivity( )<br>    Returns the Last Workflow Activity for the ePackage |
| static ePackage | getPackage(java.lang.String packageId)<br>    Returns an existing ePackage |
| static ePackage | getPackageArchive(java.lang.String packageId, java.lang.String application)<br>    Returns an existing ePackage from Archive |
| PackingList | getPackingList( )<br>    Returns an enumeration of the entire Packing List sorted by date for the ePackage. |
| int | getPriority( )<br>    Returns the priority setting for the ePackage (High, Medium Low, Stat) |
| int | getQueue( )<br>    Returns the queue for the ePackage (In, Out, Error) |
| java.util.Date | getReceivedDate( )<br>    Returns the date and time received for the ePackage |
| java.util.Date | getSentDate( )<br>    Returns the date and time sent for the ePackage |
| Source | getSource( )<br>    Returns the source object for the ePackage. |
| TrackingHistory | getTrackingHistory( )<br>    Returns an enumeration of the entire Tracking History sorted by date for the ePackage. |
| WorkflowActivity | getWorkflowActivity(java.lang.String key)<br>    Returns an individual Workflow Activity object by passing in its internal key. |

| | Method Summary | |
|---|---|---|
| WorkflowHistory | getWorkflowHistory( ) Returns an enumeration of the entire Workflow History sorted by date for the ePackage. | |
| static void | putPackage(ePackage epackage) Saves an existing ePackage | |
| static void | putPackageArchive(ePackage epackage, java.lang.String application) Saves an existing ePackage to Archive | |
| void | remove(Item item) Removes a Packing List Item object from the ePackage. | |
| void | remove(TrackingActivity trackingActivity) Removes a Tracking Activity object from the ePackage. | |
| void | remove(WorkflowActivity workflowActivity) Removes a Workflow Activity object from the ePackage | |
| static void | removePackage(ePackage epackage) Removes an existing ePackage | |
| static void | removePackageArchive(ePackage epackage, java.lang.String application) Removes an existing ePackage from Archive | |
| static void | reply(ePackage epackage) Deprecated | |
| static void | send(ePackage epackage) Submits an ePackage to the out box store for subsequent delivery to its destination. | |
| void | setCreationDate(java.util.Date date) Sets the create date and time for the ePackage | |
| void | setDestination(Destination src) Sets the destination object for the ePackage. | |
| java.lang.String | setId(java.lang.String id) Sets the globally unique package identifier for the ePack | |
| void | setLastStoredDate(java.util.Date date) Sets the date and time last saved for the ePackage | |
| void | setPriority(int priority) Sets the priority setting for the ePackage (High, Medium Low, Stat) | |
| void | setQueue(int queue) Sets the queue for the ePackage (In, Out, Error) | |
| void | setReceivedDate(java.util.Date date) Sets the date and time received for the ePackage | |
| void | setSentDate(java.util.Date date) Sets the date and time sent for the ePackage | |
| void | setSource(Source src) Sets the source object for the ePackage. | |

| Methods inherited from class java.lang.Object |
|---|
| clone, equals, finalize, getClass, hashCode, notify, notifyAll, toString, wait, wait, wait |

| Field Detail |
|---|
| 6.1.1 _VERSION |
| public static final java.lang.String _VERSION |
| 6.1.2 _EPACKAGE |
| public static final java.lang.String _EPACKAGE |
| 6.1.3 _CREATIONDATE |
| public static final java.lang.String _CREATIONDATE |
| 6.1.4 _LASTSTOREDDATE |
| public static final java.lang.String _LASTSTOREDDATE |
| 6.1.5 _SOURCE |
| public static final java.lang.String _SOURCE |
| 6.1.6 _DESTINATION |
| public static final java.lang.String _DESTINATION |
| 6.1.7 _APPLICATION |
| public static final java.lang.String _APPLICATION |
| 6.1.8 _PACKAGES |
| public static final java.lang.String _PACKAGES |
| 6.1.9 _QUEUE |
| public static final java.lang.String _QUEUE |
| 6.1.10 _PRIORITY |
| public static final java.lang.String _PRIORITY |
| 6.1.11 NONE |
| public static final int NONE |
| 6.1.12 IN |
| public static final int IN |
| 6.1.13 OUT |
| public static final int OUT |
| 6.1.14 ERROR |
| public static final int ERROR |

| Constructor Detail |
| --- |
| 6.1.15    ePackage<br>public ePackage( )<br>    throws java.lang.Exception<br>Default constructor<br>6.1.16    ePackage<br>public ePackage(ePackage epackage)<br>    Copy Constructor |

-continued

| Constructor Detail |
| --- |
| 6.1.17    ePackage<br>public ePackage(Source src,<br>    Destination dest)<br>    throws java.lang.Exception<br>Constructor used to create a new ePackage when the Source<br>and Destination objects are supplied. |

| Method Detail |
| --- |
| 6.1.18    getPackage<br>public static ePackage getPackage(java.lang.String packageId)<br>    throws java.lang.Exception<br>Returns an existing ePackage<br>6.1.19    putPackage<br>public static void putPackage(ePackage epackage)<br>    throws java.lang.Exception<br>Saves an existing ePackage<br>6.1.20    removePackage<br>public static void removePackage(ePackage epackage)<br>    throws java.lang.Exception<br>Removes an existing ePackage<br>6.1.21    getPackageArchive<br>public static ePackage getPackageArchive(java.lang.String packageId,<br>    java.lang.String application)<br>    throws java.lang.Exception<br>Returns an existing ePackage from Archive<br>6.1.22    putPackageArchive<br>public static void putPackageArchive(ePackage epackage,<br>    java.lang.String application)<br>    throws java.lang.Exception<br>Saves an existing ePackage to Archive<br>6.1.23    removePackageArchive<br>public static void removePackageArchive(ePackage epackage,<br>    java.lang.String application)<br>    throws java.lang.Exception<br>Removes an existing ePackage from Archive<br>6.1.24    send<br>public static void send(epackage epackage)<br>    throws java.lang.Exception<br>Submits an ePackage to the out box store for subsequent delivery to its destination. The Tracking<br>History is updated and a route is determined depending on the state of the ePackage.<br>6.1.25    reply<br>public static void reply(ePackage epackage)<br>    throws java.lang.Exception<br>Deprecated<br>6.1.26    getCreationDate<br>public java.util.Date getCreationDate( )<br>    Returns the create date and time for the ePackage<br>6.1.27    setCreationDate<br>public void setCreationDate(java.util.Date date)<br>    Sets the create date and time for the ePackage<br>6.1.28    getSentDate<br>public java.util.Date getSentDate( )<br>    Returns the date and time sent for the ePackage<br>6.1.29    setSentDate<br>public void setSentDate(java.util.Date date)<br>    Sets the date and time sent for the ePackage<br>6.1.30    getReceivedDate<br>public java.util.Date getReceivedDate( )<br>    Returns the date and time received for the ePackage<br>6.1.31    setReceivedDate<br>public void setReceivedDate(java.util.Date date)<br>    Sets the date and time received for the ePackage<br>6.1.32    getLastStoredDate<br>public java.util.Date getLastStoredDate( )<br>    Returns the date and time last saved for the ePackage<br>6.1.33    setLastStoredDate<br>public void setLastStoredDate(java.util.Date date)<br>    Sets the date and time last saved for the ePackage |

| Method Detail -continued |
| --- |

6.1.34 getPriority
public int getPriority( )
    Returns the priority setting for the ePackage(High, Medium, Low, Stat)
    6.1.35    setPriority
public void setPriority(int priority)
    Sets the priority setting for the ePackage(High, Medium, Low, Stat)
    6.1.36    getId
public java.lang.String getId( )
    Returns the globally unique package identifier for the ePackage
    6.1.37    setId
public java.lang.String setId(java.lang.String id)
    Sets the globally unique package identifier for the ePackage
    6.1.38    getQueue
public int getQueue( )
    Returns the queue for the ePackage(In, Out, Error)
    6.1.39    setQueue
public void setQueue(int queue)
    Sets the queue for the ePackage(In, Out, Error)
    6.1.40    getSource
public Source getSource( )
    Returns the source object for the ePackage. This is the node/organization from which the ePackage
    originates.
    6.1.41    setSource
public void setSource(Source src)
    Sets the source object for the ePackage. This is the node/organization from which the ePackage
    originates.
    6.1.42    getDestination
public Destination getDestination( )
    Returns the destination object for the ePackage. This is the node/organization from which the
    ePackage is to be delivered.
    6.1.43    setDestination
public void setDestination(Destination src)
    Sets the destination object for the ePackage. This is the node/organization from which the ePackage
    is to be delivered.
    6.1.44    add
public java.lang.String add(TrackingActivity trackingActivity)
        throws java.lang.Exception
    Adds or updates a Tracking Activity object for the ePackage. It returns an internally generated key
    which can be used later to access an individual object. The Tracking Activity object is managed
    internally by the ePackage infrastructure.
    6.1.45    remove
public void remove(TrackingActivity trackingActivity)
        throws java.lang.Exception
    Removes a Tracking Activity object from the ePackage.
    6.1.46    getTrackingHistory
public TrackingHistory getTrackingHistory( )
    Returns an enumeration of the entire Tracking History sorted by date for the ePackage.
    6.1.47    getLastTrackingActivity
public TrackingActivity getLastTrackingActivity( )
    Returns the Last Tracking Activity for the ePackage
    6.1.48    add
public java.lang.String add(WorkflowActivity workflowActivity)
        throws java.lang.Exception
    Adds or updates a Workflow Activity object for the ePackage. It returns an internally generated key
    which can be used later to access an individual object. The Workflow Activity object is managed by
    the application.
    6.1.49    getWorkflowActivity
public WorkflowActivity getWorkflowActivity(java.lang.String key)
            throws java.lang.Exception
    Returns an individual Workflow Activity object by passing in its internal key.
    6.1.50    remove
public void remove(WorkflowActivity workflowActivity)
       throws java.lang.Exception
    Removes a Workflow Activity object from the ePackage.
    6.1.51    getWorkflowHistory
public WorkflowHistory getWorkflowHistory( )
    Returns an enumeration of the entire Workflow History sorted by date for the ePackage.
    6.1.52    getLastWorkflowActivity
public WorkflowActivity getLastWorkflowActivity( )
    Returns the Last Workflow Activity for the ePackage
    6.1.53    add
public java.lang.String add(Item item)
        throws java.lang.Exception
    Adds or updates a Packing List Item object for the ePackage. It returns an internally generated key
    which can be used later to access an individual object. The Packing List object is managed by the
    application.

-continued

| Method Detail |
|---|
| 6.1.54     getItem |
| public Item getItem(java.lang.String key) |
|        throws java.lang.Exception |
|      Returns an individual Packing List Item object by passing in its internal key. |
| 6.1.55     remove |
| public void remove(Item item) |
|        throws java.lang.Exception |
|      Removes a Packing List Item object from the ePackage. |
| 6.1.56     getPackingList |
| public PackingList getPackingList( ) |
|      Returns an enumeration of the entire Packing List sorted by date for the ePackage. |
| 6.1.57     getLastItem |
| public Item getLastItem( ) |
|      Returns the Last item for the ePackage |
| 6.1.58     getIndexCollection |
| public com.mckesson.util.io.index.Index[ ] getIndexCollection( ) |
|      Specified by: |
|      getIndexCollection in interface com.mckesson.util.io.index.Indexable |
| Overview Package    Class Tree Deprecated Index Help |
| PREV CLASS NEXT CLASS                 FRAMES NO FRAMES |
| SUMMARY: INNER\|FIELD\|CONSTR\|METHOD     DETAIL: FIELD\|CONSTR\|METHOD |

Preferred Embodiments of the Present Invention

Figure 8:
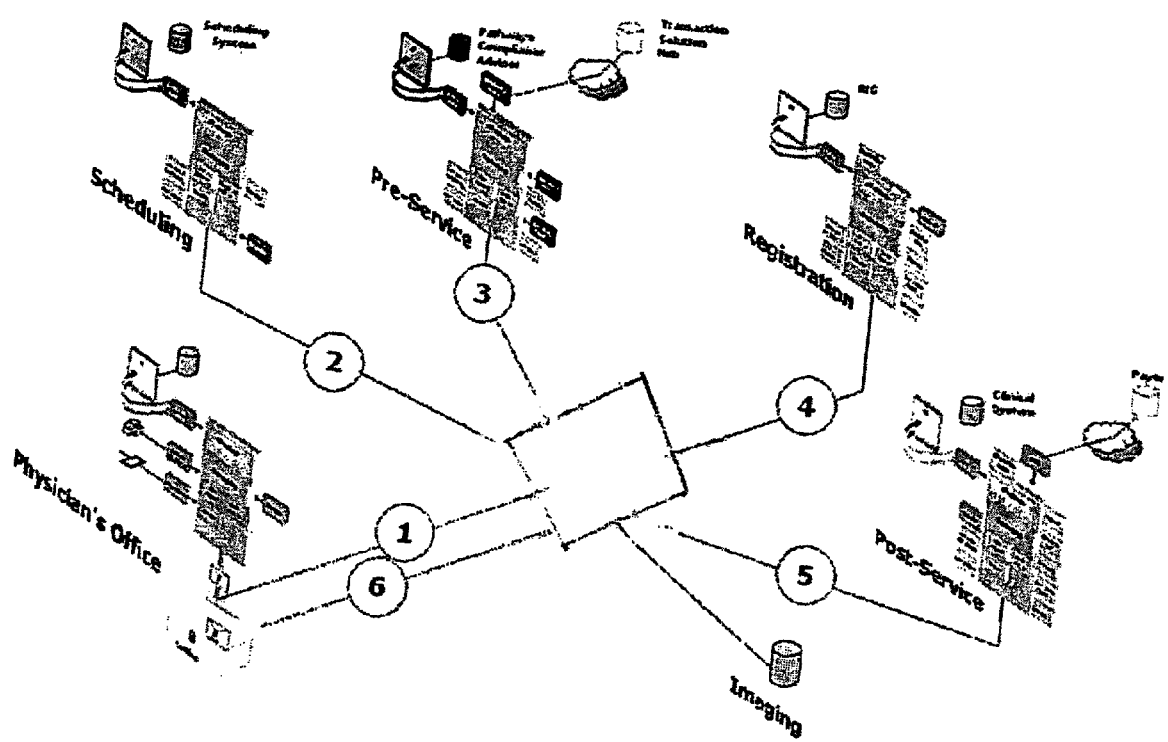
FIG. 8 shows an embodiment of the present invention which utilizes the ePackage.

FIG. 8 shows one embodiment of the present invention in which incorporates the ePackage as described above. First, a physician office 100 requests a health care service from a hospital provider. The process starts at the physician office where the office staff fills out a request for service form. This form is submitted to the hospital's node and an ePackage is constructed and stored in the hospital's node database. It should be noted that the communication to the hospital's nodes is done securely via the hospital's Virtual Private Network ("VPN"). As will also be discussed hereinafter with respect to screen shots, the patient demographics are added from the physician's practice management system into the ePackage using commercially available screen scraping techniques. Licensed Diagnostic/procedure codes are then selected from embedded tables in the ePackage form. Images, such as drivers license and insurance card scans, may be added to the ePackage.

Schedule request information (preferred date, time, who to contact, etc.) is added to the ePackage. Such schedule request information may include the patient's preferred date and time for her/his appointment, contact information, etc. In some embodiments, the ePackage form is signed (via electronic signature) and saved into the hospital's node using the Infrastructure.

Referring to FIG. 8, the ePackage is then delivered over the Infrastructure to the hospital provider. The ePackage may be accessed from a worklist in scheduling. The worklist is filtered to sort on specific ePackages. Scheduling data can be utilized by a scheduling system using commercially-available screen-scraping techniques, known to one of ordinary skill in the art.

The scheduling data in the ePackage may be compared to the available schedule at the hospital and physician performing the desired procedure. The schedule result data can be pulled into the ePackage using screen-scraping techniques.

At this point, the ePackage is updated with new scheduling information (when the patient is scheduled, where, etc.). Pre-Service personnel at the hospital then access the ePackage from their worklist. Eligibility may be checked through a secure web service call to an eligibility provider. Further, new information (ABN, authorization or pre-cert number, co-pay amount, etc.) may be added to the ePackage.

After the above steps have been performed, the ePackage is available at hospital registration and all interested nodes with all of the required information. An order number may also be added to the ePackage to identify the result information.

The patient may then attend the appointment during which the desired hospital service is performed. When the service is complete, the result information may be added to the ePackage and returned to the referring physician.

Figure 10:
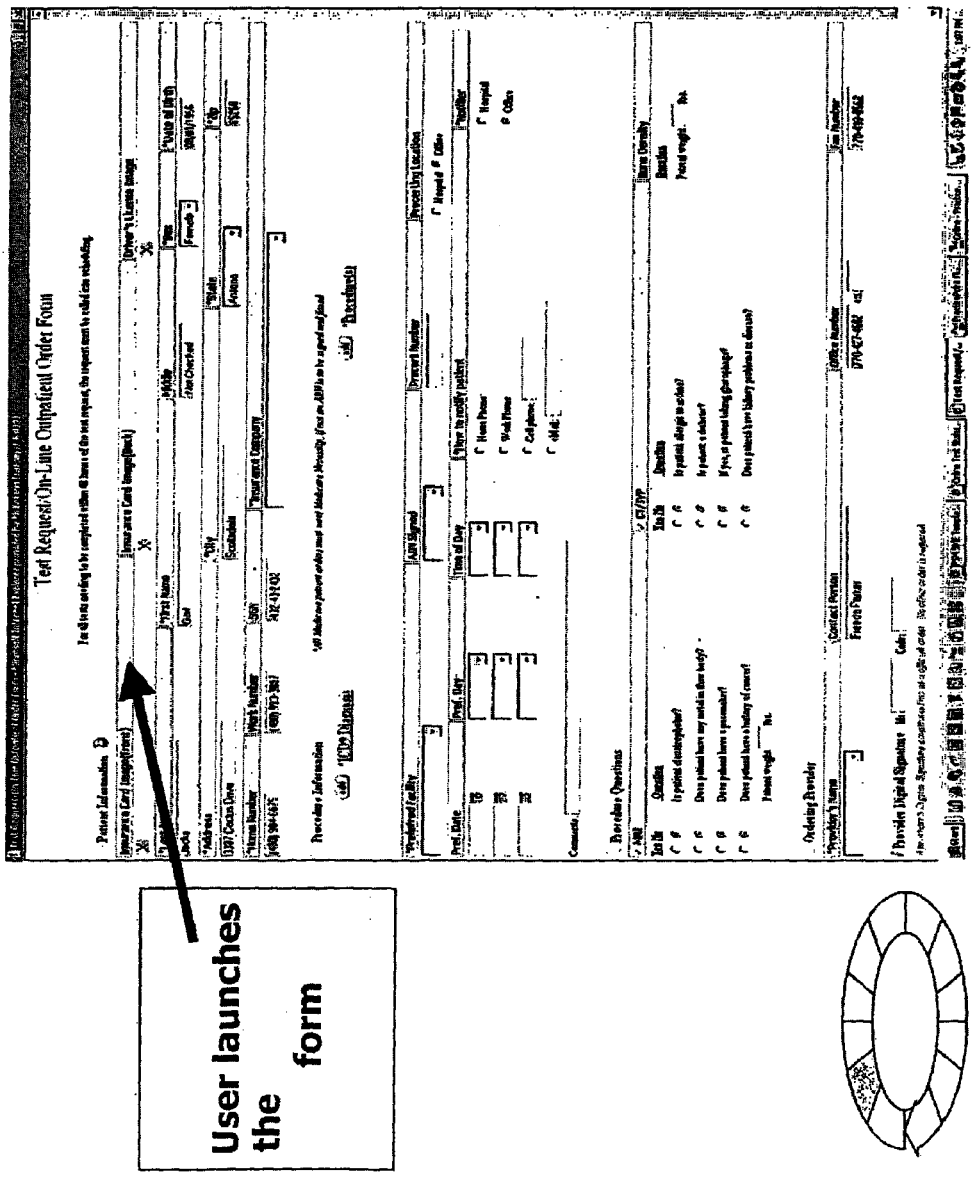

FIGS. 9-26 provide exemplary screen shots of the steps described above. FIGS. 9-13 detail the step of collecting patient information, e.g., by the physician office staff. FIG. 9 shows a screen shot seen by a user at the physician office staff when entering patient information. In this case, the patient is Gail Jacks. Personal Information such as address, employer, social security number, etc. is entered. FIG. 10 depicts the screen shot once the user has launched the ePackage form. As can be seen, in this embodiment, the ePackage form includes information, such as insurance provider, preferred facility, preferred scheduling dates and times, as well as other procure questions detailed on the screen shot.

FIG. 11 shows a screen shot prior to data entry. In this embodiment, the requested data may be inputted manually, or in other embodiments, the data may be moved from the physician's practice management application directly into the ePackage form, utilizing screen scraper technology or other forms of data transfer known to one of ordinary skill in the art having the benefit of this disclosure.

FIG. 12 shows an embodiment of the present invention in which digital scans of insurance cards and drivers' licenses may be added to the ePackage via any TWAIN-complaint scanner. In this way, valuable information may be captured from the physician's office for later use. Additionally, voice annotations may be included as attachments to the ePackage. Many types of stored images may be included as attachments to the ePackage, in addition to screen captures. Once the information has been collected, the user presses the submit key, or may cancel the operation.

Figure 13:
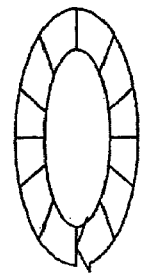

FIG. 13 shows a screen shot of an embodiment in which a patient's driver's license and health insurance card have been digitally captured to be added to the ePackage.

Once the patient information is collected, the user may then select diagnosis codes or search the codes by description as shown in the screen shot of FIG. 14. Multiple codes may be added to any one request form if needed. Codes may be uploaded from hospital flat files, which reduces transposition errors and the time required by the user to enter the correct code.

Figure 15:
Figure 16:
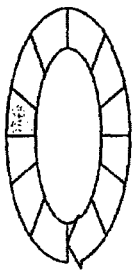

The patient's preferred dates, times, and locations, etc. for the required procedure is then entered on the ePackage form by the user as shown in the screen shot of FIG. 15. As shown in FIG. 16, in some embodiments, a pop-up calendar allows for selection of the preferred day and time for the procedure. Patient contact information may also be included.

In this embodiment, the user may also enter comments onto the ePackage, as shown in the screen shot of FIG. 17. Further, anyone later accessing the ePackage may include notes in the comments field. For instance, physicians and staff can enter patient detail or special requests, scheduling can add pre-test instructions and materials, and Pre-Service personnel can ask questions and obtain further information. The comments text entry box enables threaded communications throughout the life of the ePackage.

Figure 18:
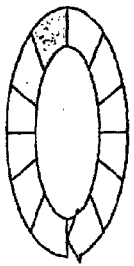

As shown in the screen shot of FIG. 18, the requesting physician's electronic signature may then be applied to the ePackage form, so that the physician's signature is obtained prior to the patient's arrival at the hospital.

Once complete, the epackage may be submitted. Each ePackage that has been submitted may then appear on a physician's worklist. For example, as shown on the screen shot of FIG. 19, a worklist for "Marietta Internal Medicine" is shown. As shown, the worklist includes the patient name, date of birth, procedure to be performed, physician, status, date requested, date scheduled, and facility. The physician staff can view the status and updates made to any particular ePackage.

Figure 20:
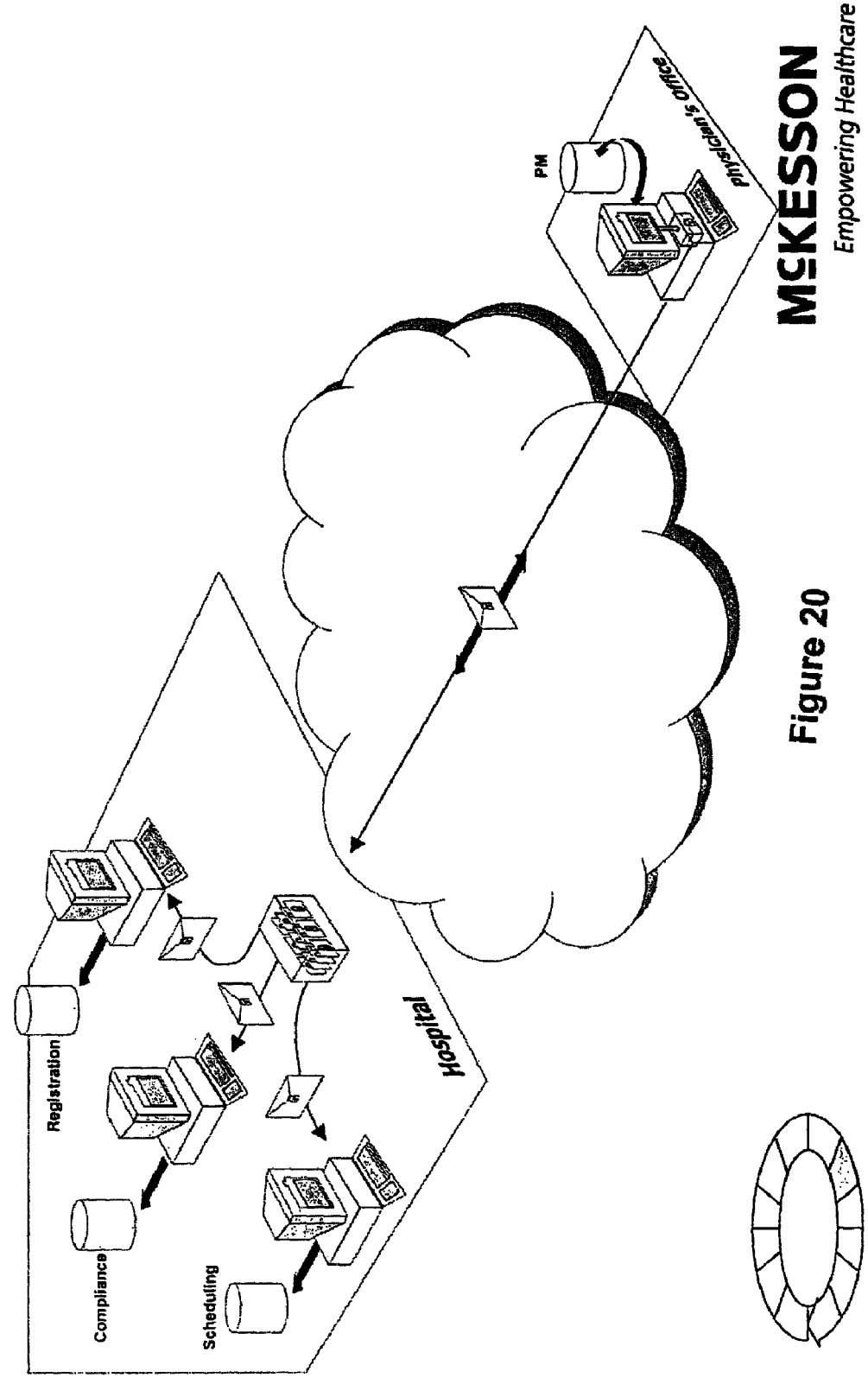

The ePackages are saved to the hospital's node via the peer-to-peer infrastructure (as described above) or by the physician's office accessing the hospital's centralized server, via VPN, for example. This submission is shown in FIG. 20.

The hospital may then view its worklist as shown in the screen shot of FIG. 21. For instance, the hospital scheduler may filter the worklist to show requests requiring scheduled attention. The scheduler may then access the ePackage or choice to perform the scheduling operation. Once a patient has been selected, that patient's ePackage information appears. Once a user has accessed a request for radiology service form, the other users of the system are locked out of that particular form until it has been unlocked.

Figure 22:
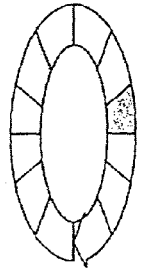

FIG. 22 shows a screen shot available to the hospital scheduler on a particular package has selected. The ePackage data may be transferred from the ePackage into the hospital's scheduling database via screen scraping technology, as shown in FIG. 23. The hospital's scheduling database may then compare the patient's preferred schedule for the procedure to those time available for the procedure. The resulting appointment time and scheduling information may then be transferred from the hospital's scheduling database directly into the ePackage, as shown in the screen shot of FIG. 24.

In some embodiments, Pre-Service checks may be performed. For instance, in the screen shot of FIG. 25, eligibility of benefits may be verified in a manner similar to the scheduling operation described above. That is, the patient's information (e.g. insurance) may be transferred into an eligibility database, compared to that database, and the eligibility information then inserted into the ePackage. In some embodiments, the ePackage may be used to perform medical necessity and code audits, and to provide an advance beneficiary notice (ABN). Users may print the ABN form for the patient signature at this time, as shown in the screen shot of FIG. 26.

Figure 27:
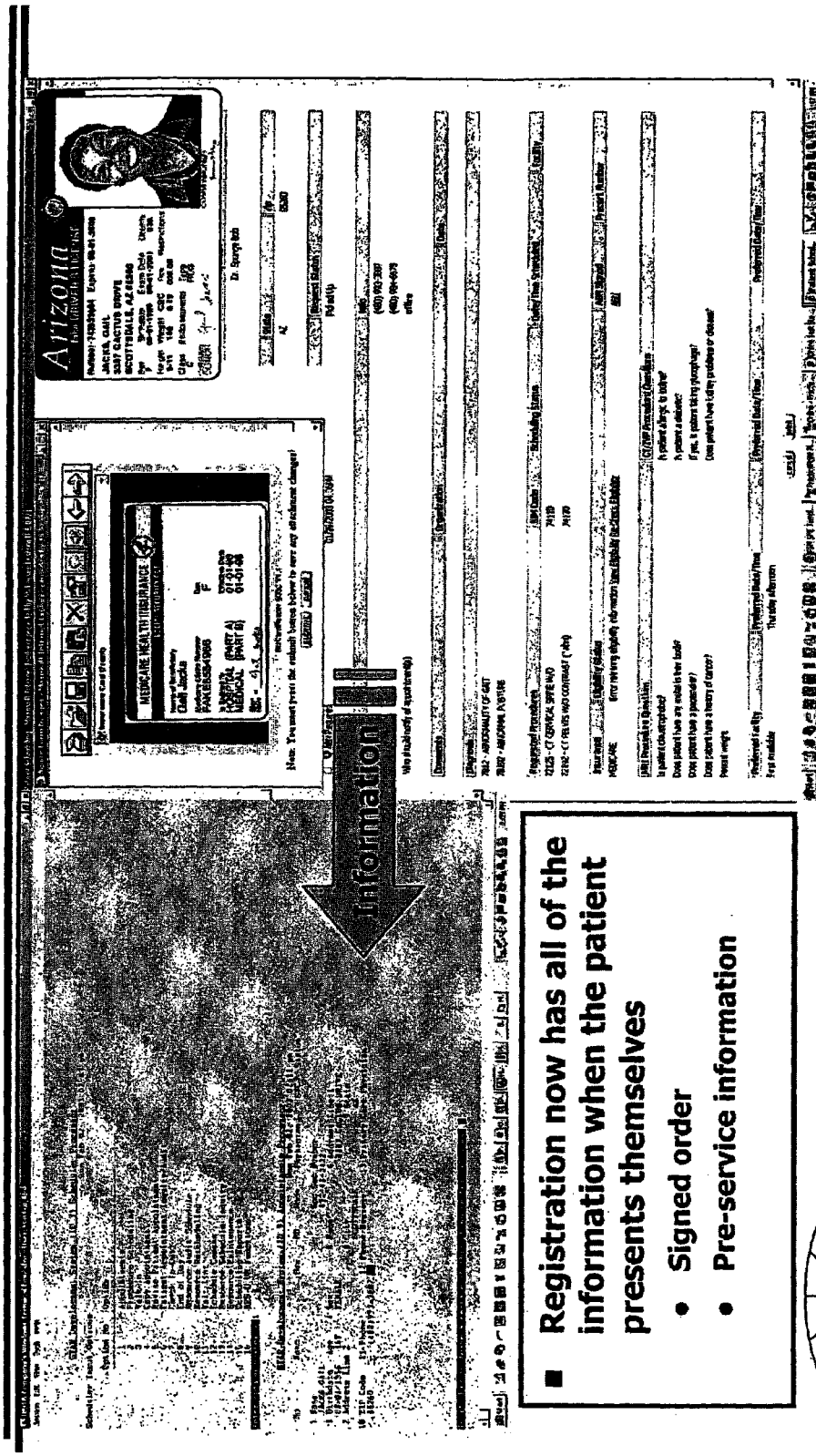

When it is time for the patient to register at the hospital for the required procedure, the hospital staff may access the ePackage. The ePackage can contain much of the required information necessary at registration, as shown in the screen shot of FIG. 27.

By utilizing the disclosed procedure, a hospital may experience multiple benefits. For instance, staff efficiency may be improved, as the number of callbacks to others for information is reduced. For instance, time in processing an order may be reduced. Further, staff may be re-deployed from telephonic/fax/paper shuffling to patient care. The hospital may contact the patient directly with schedule and pre-visit instruction. Work can be better controlled throughout the day. These advantages may increase the revenue, as more patients may be referred, denial of medical reimbursement may be decreased, productivity may be improved (by providing more services with the same staff). In short, patient service is increased, as patients may experience less delay before service.

The following is another example in which the Infrastructure and the ePackages may be utilized to facilitate patient health care. In this embodiment, the referring physician may electronically deliver a radiology request, including patient information, request forms, status updates, and results. In prior art systems, all of this information is usually transmitted via routing paper between various entities (fax, mail, courier) or a phone calls, as discussed above.

In this embodiment, two areas are of primary importance: (1) radiology request information and forms from physician practices to hospitals and (2) result information from hospital departments to a physician practice. This embodiment may be considered the primary subset of the Pre-Service system described above.

The following explains the process in detail. The order of appearance is not necessarily the sequence of events. Four "use-cases" are described hereinafter. The following definitions apply throughout this section: Originating location is the source of the radiology request, normally a physician's office. Destination location is the facility that will perform the services associated with the radiology requests, normally a hospital or clinic. Radiology requests is a set of information sent through the e-delivery system to begin the scheduling process for the requested procedures or tests. Requests communicated via this application consist of header information and pre-defined form which is presented as a .pdf file. Status is used by the e-delivery system to determine that action is required for the request.

The overall system in this embodiment functions as follows. A radiology request is produced at an originating location, typically a physician office. The radiology request typically requires a signature; therefore, in this embodiment, e-signatures are enabled. Radiology requests are routed to the appropriate destination location and recipient for processing. Senders (originating location) and receivers (destination location) of the radiology requests are able to view and change the status of the requests at various stages throughout the process. When status updates are performed for the request, the updated information is routed back to the originating location's worklist.

Figure 28:
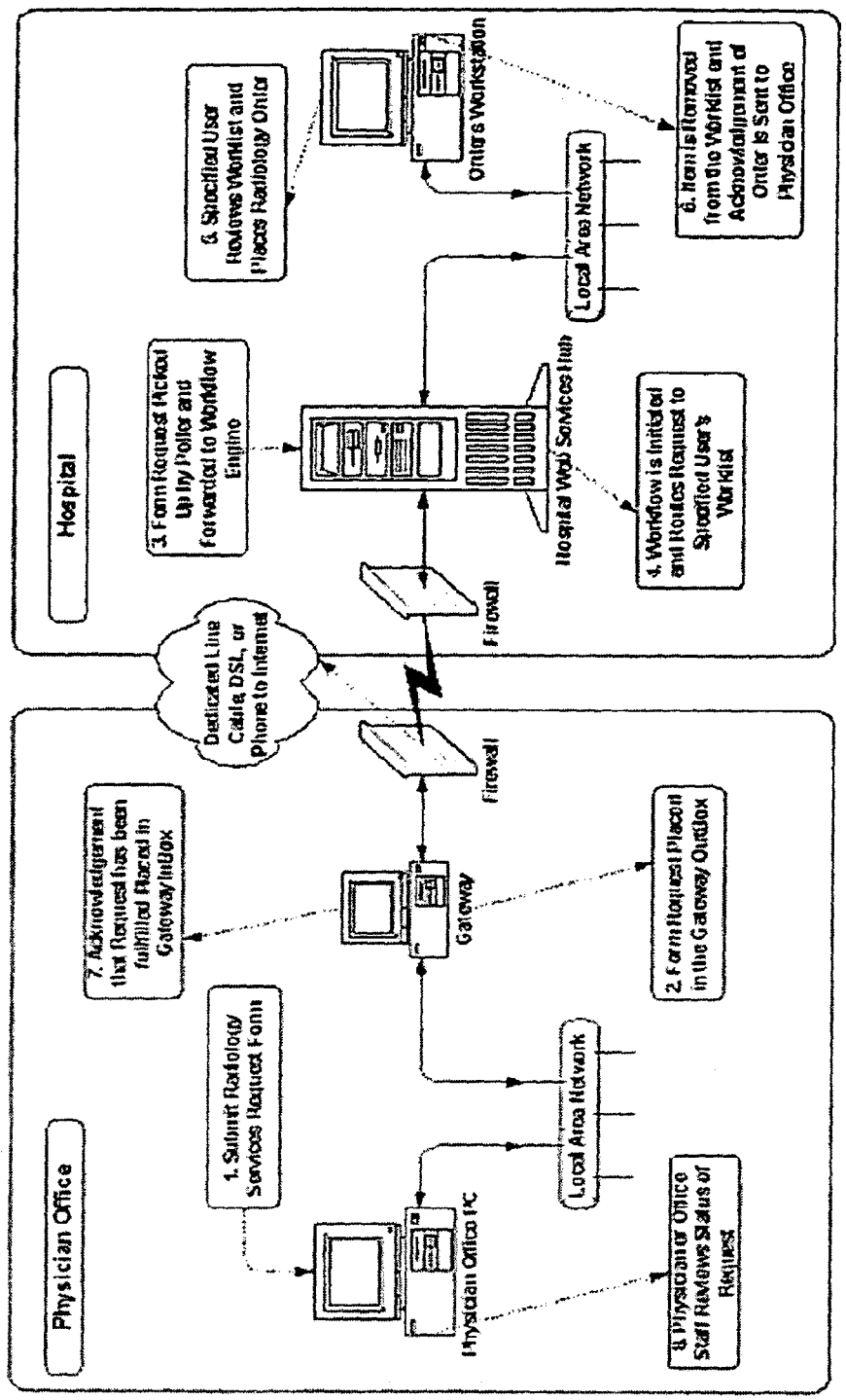
FIG. 28 shows an overall configuration of one embodiment of the present invention.

FIG. 28 shows the overall configuration of this embodiment of the present invention.

Figure 29:
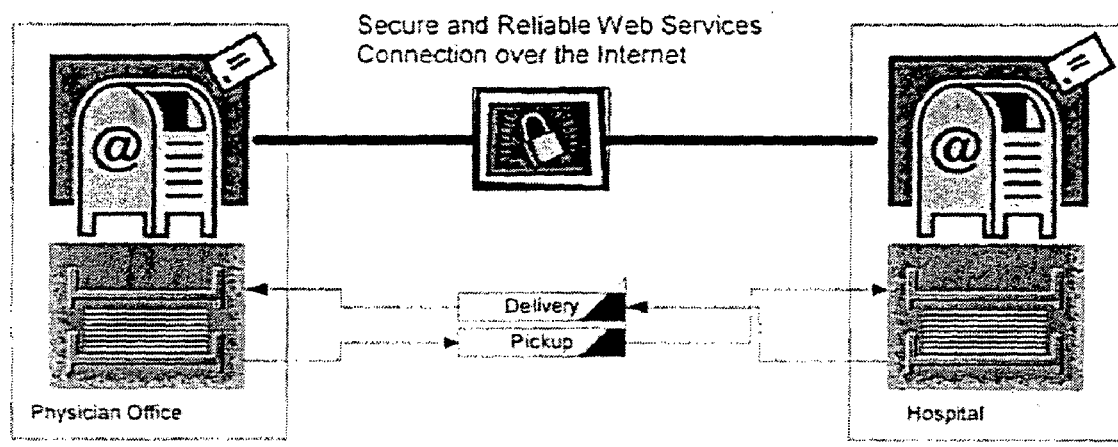
FIGS. 29-34 show an embodiment of the present invention in which a radiology request is described.

Referring to FIG. 29, one embodiment of the present invention is shown being an e-Delivery use case. As shown, requests are picked up and delivered to the appropriate nodes as well as results and status updates via the peer-to-peer infrastructure described above.

Figure 30:
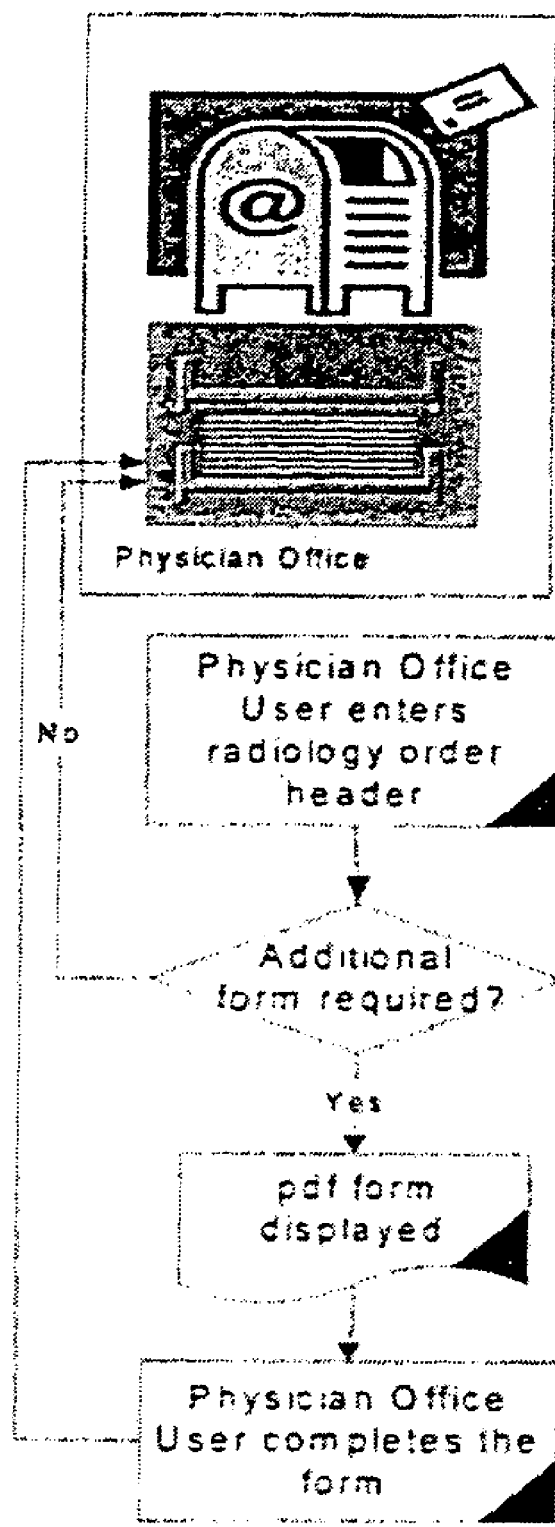

FIG. 30 shows a radiology request use case for a physician office staff uses to create a radiology request for the hospital. First, the physician office staff accesses the application on the ePackage and completes the radiology request for a patient. Radiology request headers are part of the system and include routing information (captures information necessary to send the request to the destination location, such as the physician, hospital and/or department); patient information captures information specific to the patient who will be receiving the service, e.g. name and ID); scheduling information captures information to facility scheduling between the destination location and the patient (schedule by indicator, best times to call patient, best days for appointment, best times for appointment, etc.).

Once data entry is complete, validation may be performed to ensure that all required fields are completed. If one or more required fields are blank, a message is displayed to the user.

Once validation is passed, if valid signature information was not entered into the request, it is flagged as physician signature required. The system stores an ePackage containing the request. The user may repeat the above process as needed for other patients.

Figure 31:
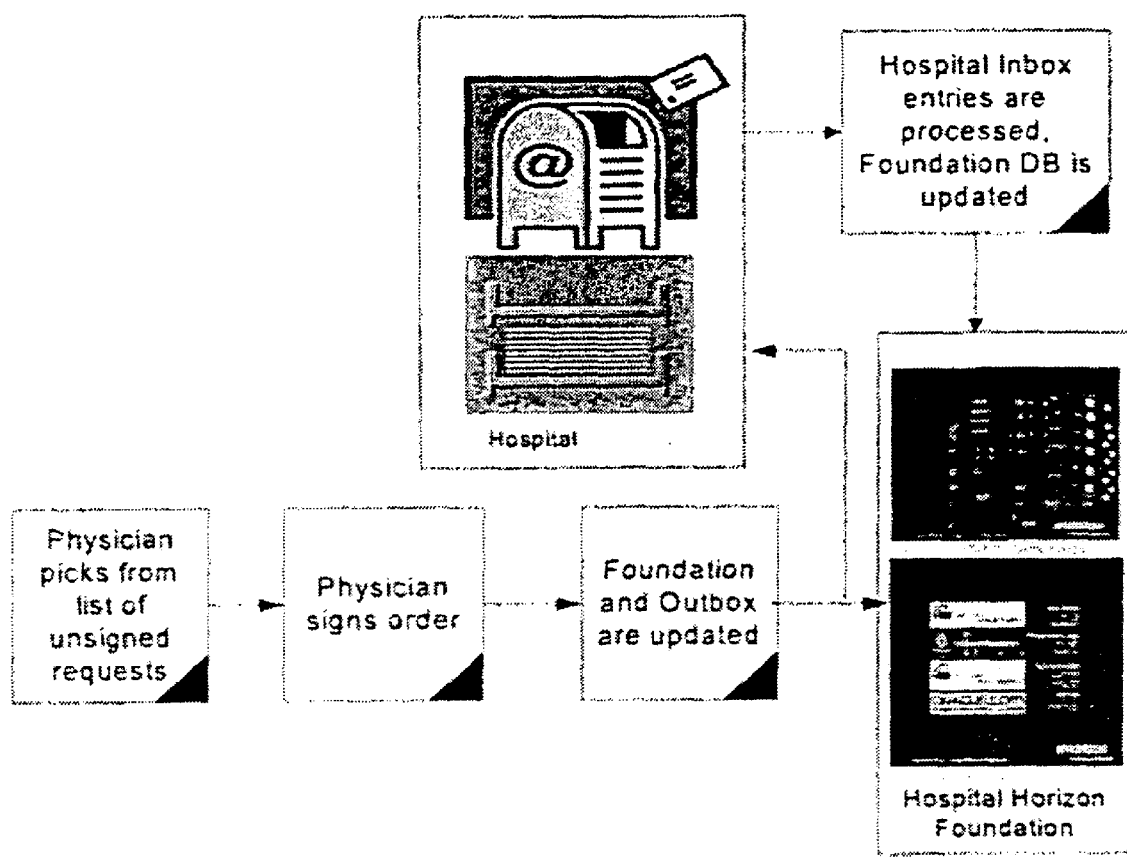

FIG. 31 shows another embodiment of the present invention in which the physicians e-signs the unsigned requests. As shown, the requests have been picked up and delivered by the e-Delivery mechanism as described above. The physician may then access the Pre-Service request worklist. The system is set up to match users with sending entity/doctor ID's on the request. The physician may then select options to receive a filtered list of unsigned requests or allow the system to display all unsigned requests found. The portal then displays unsigned requests.

At this point, the physician may select a request from the list and review the detailed request form prior to signing. When the review is complete, or if the review is necessary, the provider electronically signs the request via a pre-assigned signature, which is created in advance by the systems administrator using tools provided in the system.

The e-signature is then inserted into the request ePackage with verifiable authenticity. The status is changed to incomplete for scheduling the form not-signed alert flag is removed. These changes are reflected in the physician's office worklist. Alternatively, the user may mark a request as cancelled at any time.

Figure 32:
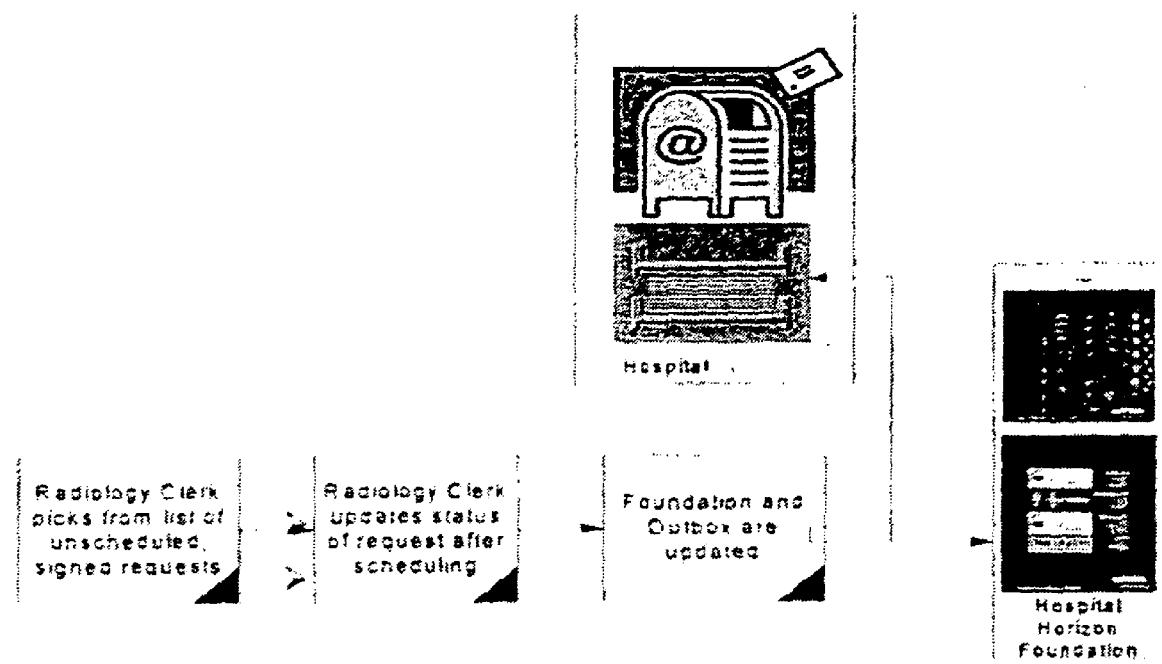

FIG. 32 details the steps for the hospital processing the requests. First, a scheduling clerk accesses the Pre-Service Manager. The system is set up to match user with destination entity/user ID's. The default view for this user is set up to display requests with a status of Incomplete. The scheduling clerk may then select the option to display requests with other criteria. The system determines if there are any requests matching the user's search criteria and displays any matching requests. Manual steps may be followed to schedule the procedure and enter the request in the request tracking system. Referring the Pre-Service Manager, the scheduling clerk may then update the request/test stated to Scheduled. Since multiple tests may be schedule from one request, this Status must reflect the aggregate status of the tests associated with the request. Alternatively, the scheduling clerk may look for Requests that have been canceled in Request to remove them from the HIS scheduling system, if they have been previously scheduled. The scheduling clerk then has the option of printing selected requests.

The physician office staff may also check the status of the Request. To do this, the physician office staff may access the Request Status Worklist and then selects the criteria to display the set of notices for their interest (or uses the default display of All requests). Updates may have occurred to these requests. The physician office staff may then sort the Requests by Request type, physician, status, date request, or patient name. The matching requests are then displayed. The physician office staff may then cancel the request.

Figure 33:
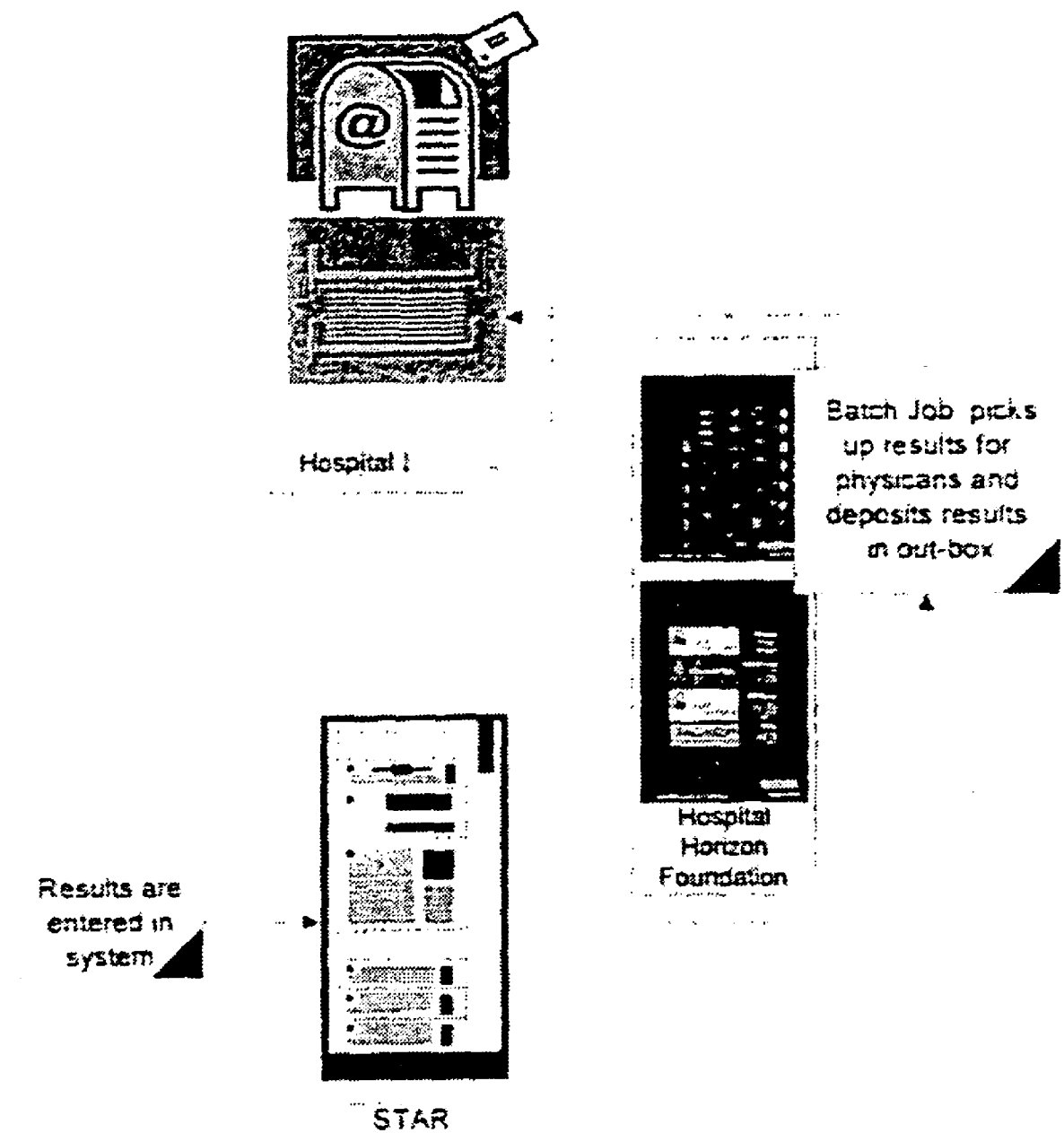

FIG. 33 shows an embodiment in which the results are collected in the hospital. As the results are entered in the Radiology or Lab system, they are queued up for delivery to physicians. Parameters may be configured on the McKesson STAR Radiology system to compile the results for configured physicians in a given practice. Compiled results are moved to appropriate data store on the hospital's node for access by the physician's office.

For administrative use, the system administrator may configure connection information for a Request node.

The system administrator may also set up the system on the origination location, e.g. the physician office/clinic. To do this, the system administrator defines valid users for that location and may assign passwords for each. Connection information for the destination location is set.

Pick list values may be selected for destination hospital, destination department, destination attention, origination office, original department, origination phone and extension, origination fax, origination requestor, origination email, requesting physician, and/or request type. Request detail forms are created and are associated with the Request Type.

Figure 34:
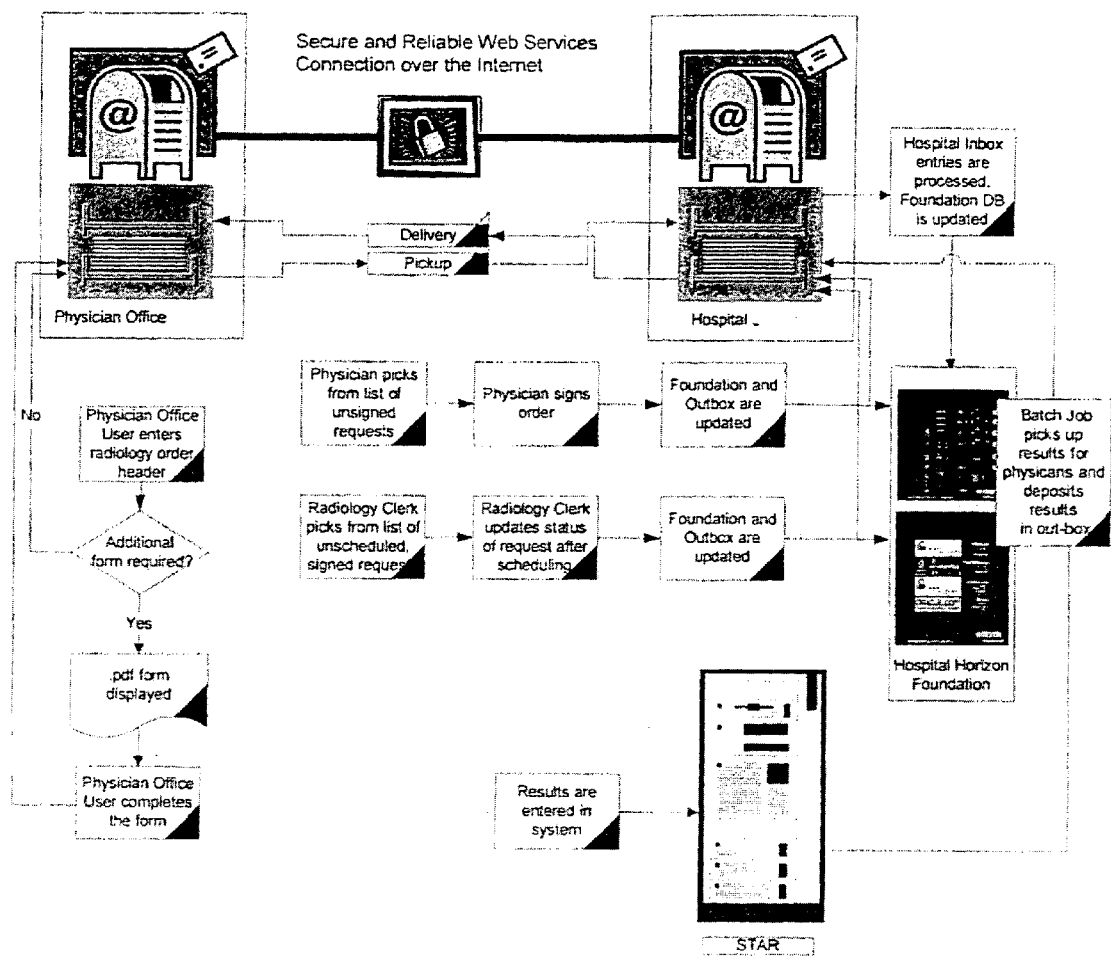

FIG. 34 shows a flow chart for the embodiment described above. Again, this is use of the invention described herein.

Although various embodiments have been shown and described, the invention is not so limited and will be understood to include all such modifications and variations as would be apparent to one skilled in the art. Specifically, although the ePackage is shown utilized with the disclosed Infrastructure, any secure network access may be utilized, such a the physician's use of the hospital's server via access over a VPN.

What is claimed is:

1. A method of improving secure communication among healthcare providers, comprising:
   receiving at a node at a healthcare provider a transmitted electronic package constructed from information requesting a health care service in a request for service form, said electronic package comprising at least package header, destination, source, tracking history, workflow history, and packing list objects, and describing the request for health care service including schedule request information and providing support content for fulfillment of the request, and wherein the electronic package was further constructed from patient information selected from the group consisting of address, employer, and social security number;
   storing the electronic package at a node database at the healthcare provider;
   accessing the electronic package via a node by the healthcare provider;
   after receiving the electronic package, comparing the schedule request information in the electronic package to a healthcare provider schedule and a schedule for a person providing the health care service to determine a mutually-compatible scheduled date for performing the requested service; and
   updating the electronic package with the scheduled date.

2. The method of claim 1, further comprising: updating the electronic package with Pre-Service information selected from the group consisting of authorization, eligibility of benefits, pre-certification number, and co-pay amounts.

3. The method of claim 1, further comprising adding an order number to the electronic package.

4. The method of claim 1, further comprising: accessing the electronic package from each of a plurality of nodes.

5. The method of claim 1, further comprising: accessing the electronic package at the healthcare provider when a patient registers for the requested service.

6. The method of claim 1, further comprising: performing the requested health care service to obtain a result; and adding the result to the electronic package.

7. The method of claim 1 wherein the patient information was entered manually.

8. The method of claim 1 wherein the patient information was digitally scanned from at least one of insurance cards and drivers' licenses.

9. The method of claim 1, wherein voice annotations were added to the electronic package.

10. The method of claim 1, further comprising updating the electronic package with diagnostic codes manually or by uploading from a hospital flat file.

11. The method of claim 1, wherein the schedule request information comprises a predetermined date, time, and location for an appointment and contact information.

12. The method of claim 11 further comprising: signing the electronic package via an electronic signature of a doctor.

13. The method of claim 1 further comprising adding comments to the electronic package.

14. The method of claim 13 in which the comments are pre-test instructions.

15. The method of claim 9, further comprising viewing the electronic package by a physician on a worklist.

16. The method of claim 15, further comprising validating to ensure that all required files in the electronic package are completed.

17. The method of claim 16, further comprising: accessing a Pre-Service request worklist; reviewing unsigned Pre-Service requests; electronically signing the Pre-Service request as an authorized signature; and inserting the authorized signature into the electronic package.

18. The method of claim 17, further comprising checking a status of the request in the electronic package by accessing a request status worklist.

19. The method of claim 1, wherein the nodes are connected via an infrastructure.

20. The method of claim 19, wherein the infrastructure comprises a peer-to-peer network or a VPN.

21. The method of claim 1, further comprising updating the electronic package with procedure codes manually or from embedded tables.

22. The method of claim 1, wherein the package header contains date information related to the electronic package; the destination contains information to which node the electronic package is to be delivered; the source contains information from which node the electronic package originates; the tracking history contains a movement log of the electronic package between the destination and source nodes; and the packing list contains a collection of item objects that contain attachments to the electronic package.

* * * * *

UNITED STATES PATENT AND TRADEMARK OFFICE
CERTIFICATE OF CORRECTION

PATENT NO.       : 7,860,726 B2                                         Page 1 of 1
APPLICATION NO.  : 10/941604
DATED            : December 28, 2010
INVENTOR(S)      : Connely, III et al.

It is certified that error appears in the above-identified patent and that said Letters Patent is hereby corrected as shown below:

<u>Title page,</u>
Item (73) Assignee: "McKesson Information Solutions LLC" should read
--McKesson Technologies Inc.--.

Signed and Sealed this
Thirty-first Day of January, 2012

David J. Kappos
*Director of the United States Patent and Trademark Office*